(12) United States Patent
Shibukawa et al.

(10) Patent No.: US 10,437,057 B2
(45) Date of Patent: Oct. 8, 2019

(54) VIRTUAL REALITY SYSTEM AND INFORMATION PROCESSING SYSTEM

(71) Applicant: Brainy Inc., Naha-shi, Okinawa (JP)

(72) Inventors: Hirofumi Shibukawa, Naha (JP); Masashi Tanaka, Naha (JP)

(73) Assignee: Brainy Inc., Naha-shi (JP)

( * ) Notice: Subject to any disclaimer, the term of this patent is extended or adjusted under 35 U.S.C. 154(b) by 17 days.

(21) Appl. No.: 15/799,900

(22) Filed: Oct. 31, 2017

(65) Prior Publication Data

US 2018/0052324 A1 Feb. 22, 2018

Related U.S. Application Data

(63) Continuation of application No. PCT/JP2016/071046, filed on Jul. 15, 2016.

(51) Int. Cl.
 *G02B 27/01* (2006.01)
 *G06F 3/01* (2006.01)
 (Continued)

(52) U.S. Cl.
 CPC ........... *G02B 27/017* (2013.01); *G06F 3/011* (2013.01); *G06F 3/0484* (2013.01); *G06F 21/32* (2013.01); *G06Q 20/40* (2013.01); *G06Q 20/40145* (2013.01); *G16H 10/60* (2018.01); *G16H 40/63* (2018.01); *G16H 50/20* (2018.01); *G02B 2027/014* (2013.01)

(58) Field of Classification Search
 None
 See application file for complete search history.

(56) References Cited

U.S. PATENT DOCUMENTS

| 8,502,780 B1 | 8/2013 | Park |
| 2008/0030461 A1* | 2/2008 | Matsui .................... G06F 3/011 |
| | | 345/156 |

(Continued)

FOREIGN PATENT DOCUMENTS

| JP | 2015118556 A | 6/2015 |
| JP | 2015230236 A | 12/2015 |

(Continued)

OTHER PUBLICATIONS

Japan Patent Office, Notice of Allowance Issued in Application No. JP2016-567869, dated Jan. 17, 2017, 6 pages.
(Continued)

*Primary Examiner* — Matthew Yeung
(74) *Attorney, Agent, or Firm* — McCoy Russell LLP

(57) ABSTRACT

A virtual reality system includes a first information processing device, a virtual reality headset, a biometric data acquisition device, a first sensor, and a second sensor. The first information processing device creates virtual reality content. The virtual reality headset is worn by the user and displays the virtual reality content received from the first information processing device to the user. The biometric data acquisition device acquires biometric data of the user. The first information processing device adds an image making the user recognize the position and the direction of the biometric data acquisition device to the virtual reality content on the basis of position and direction information created by the first sensor and the second sensor.

8 Claims, 18 Drawing Sheets

(51) Int. Cl.
*G06Q 20/40* (2012.01)
*G06F 21/32* (2013.01)
*G06F 3/0484* (2013.01)
*G16H 40/63* (2018.01)
*G16H 10/60* (2018.01)
*G16H 50/20* (2018.01)

(56) References Cited

U.S. PATENT DOCUMENTS

| | | |
|---|---|---|
| 2014/0139439 A1 | 5/2014 | Park |
| 2015/0142596 A1* | 5/2015 | Jakobson ............ G06Q 20/085 705/24 |
| 2015/0278498 A1 | 10/2015 | Hong et al. |
| 2015/0358778 A1 | 12/2015 | Heo et al. |
| 2016/0358181 A1* | 12/2016 | Bradski ............ G06Q 20/40145 |
| 2017/0228710 A1* | 8/2017 | Lee ........................ G06Q 20/32 |

FOREIGN PATENT DOCUMENTS

| | | |
|---|---|---|
| JP | 2016506530 A | 3/2016 |
| WO | 2015016524 A1 | 2/2015 |

OTHER PUBLICATIONS

European Patent Office, Extended European Search Report Issued in Application No. 16899690.8, dated Oct. 17, 2018, Germany, 10 pages.

* cited by examiner

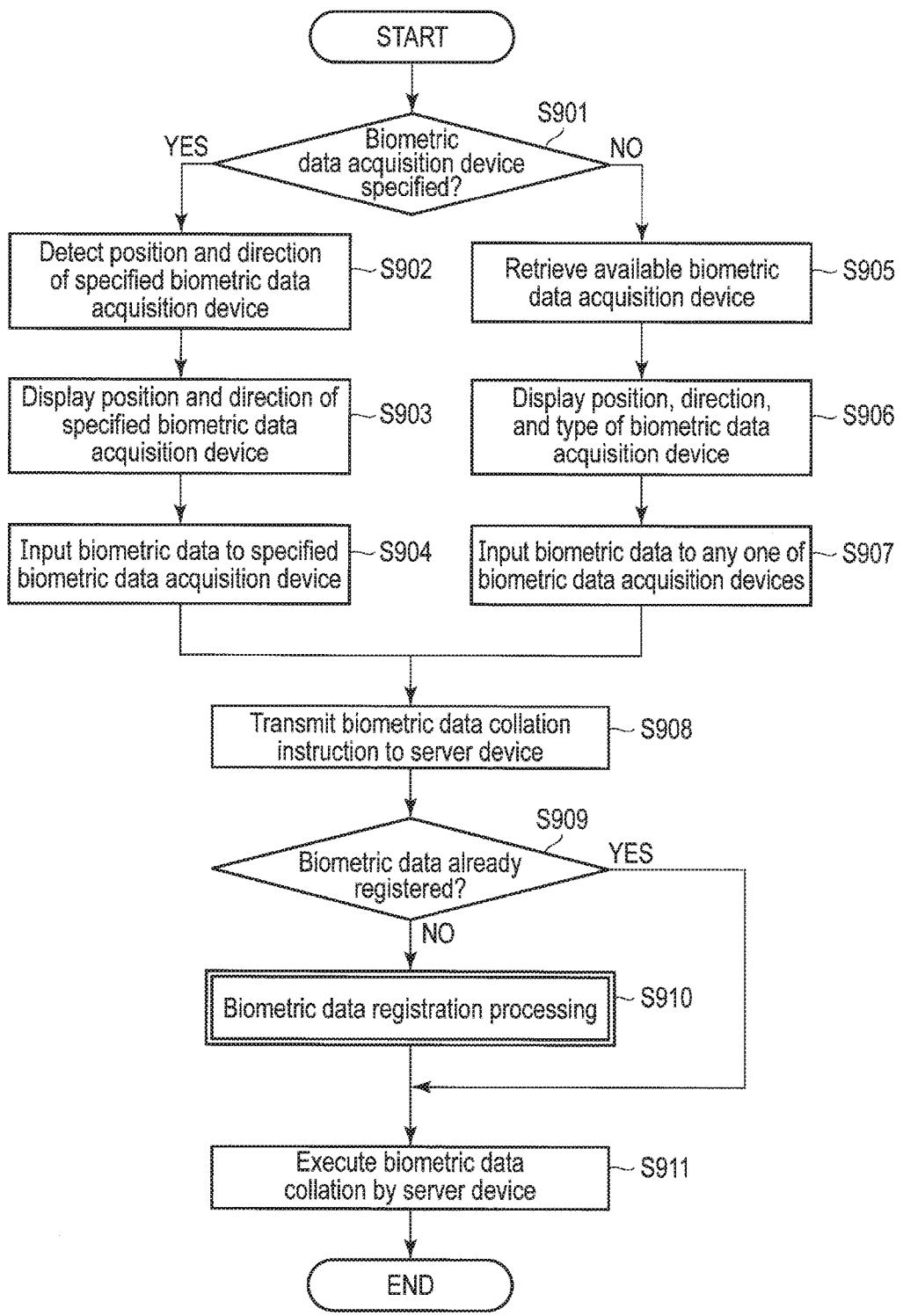
F I G. 9

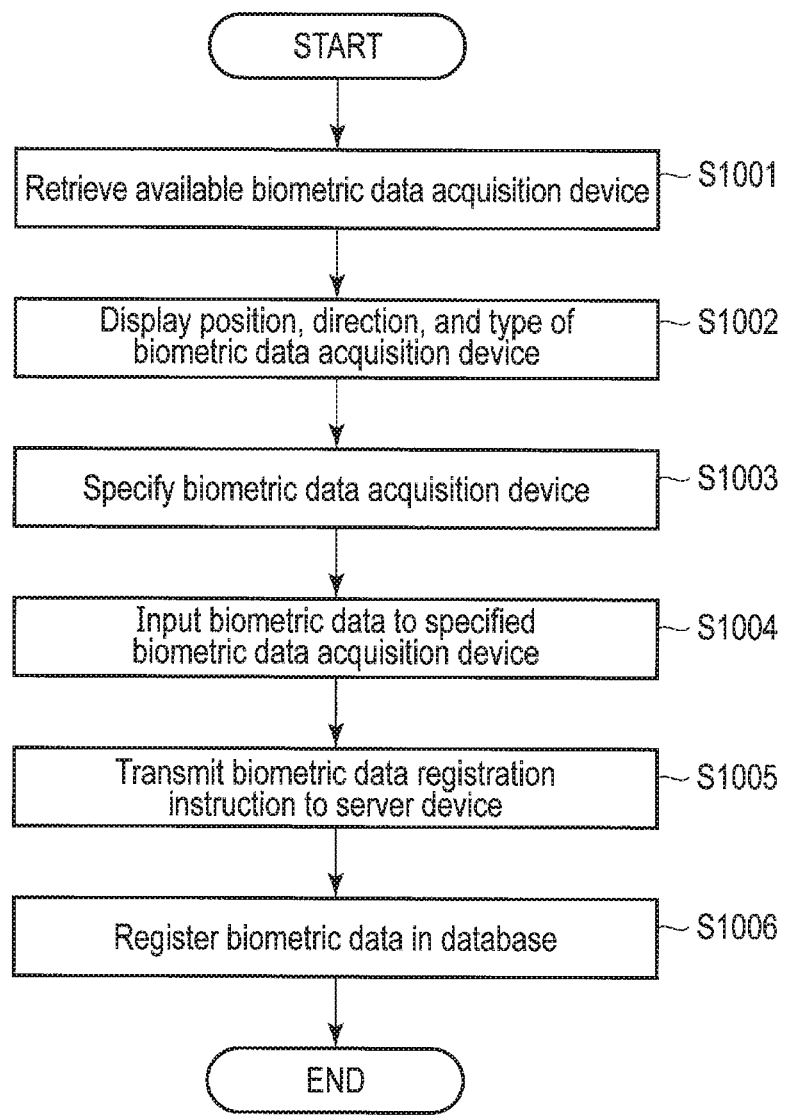
F I G. 10

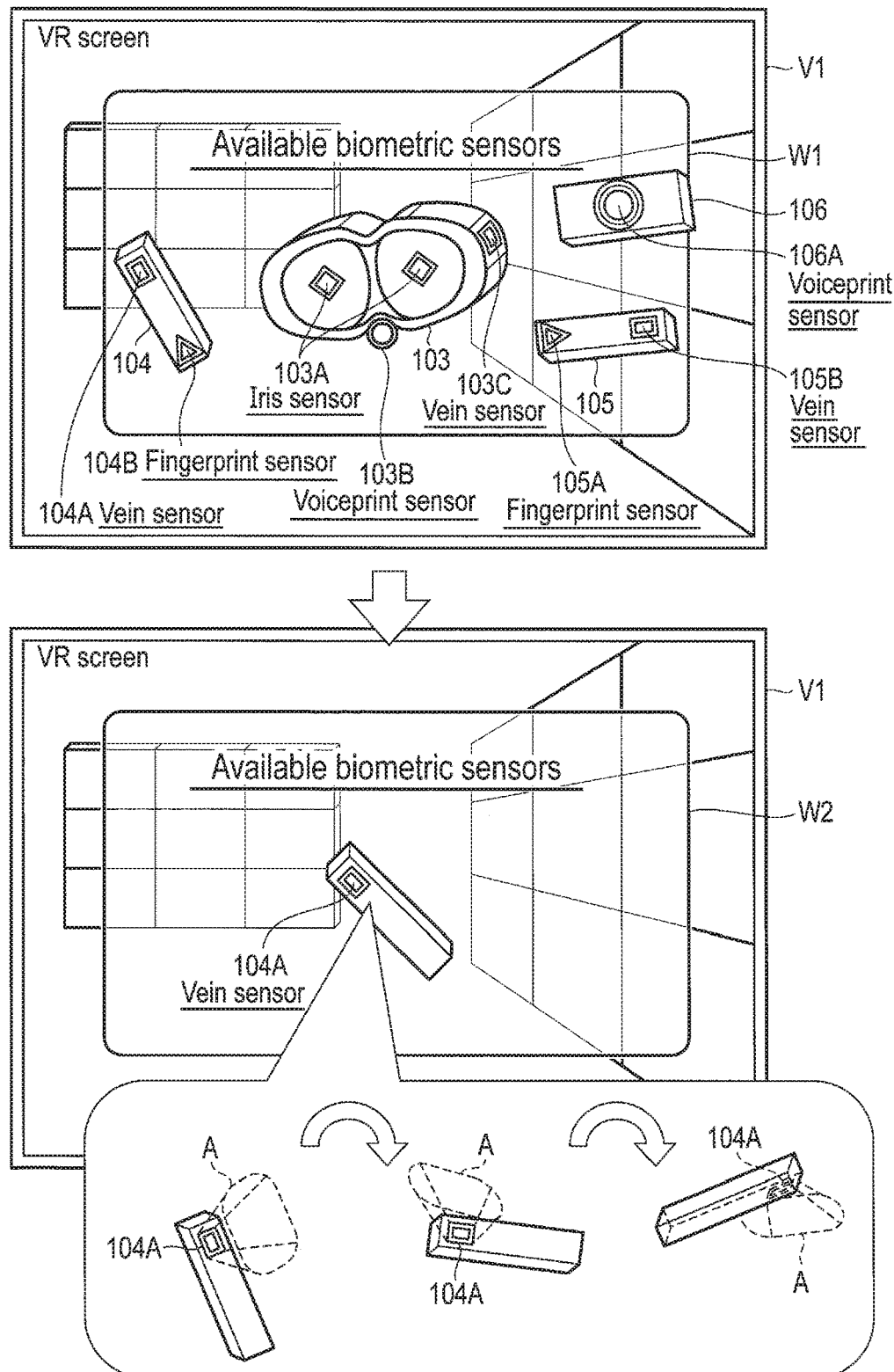
F I G. 11

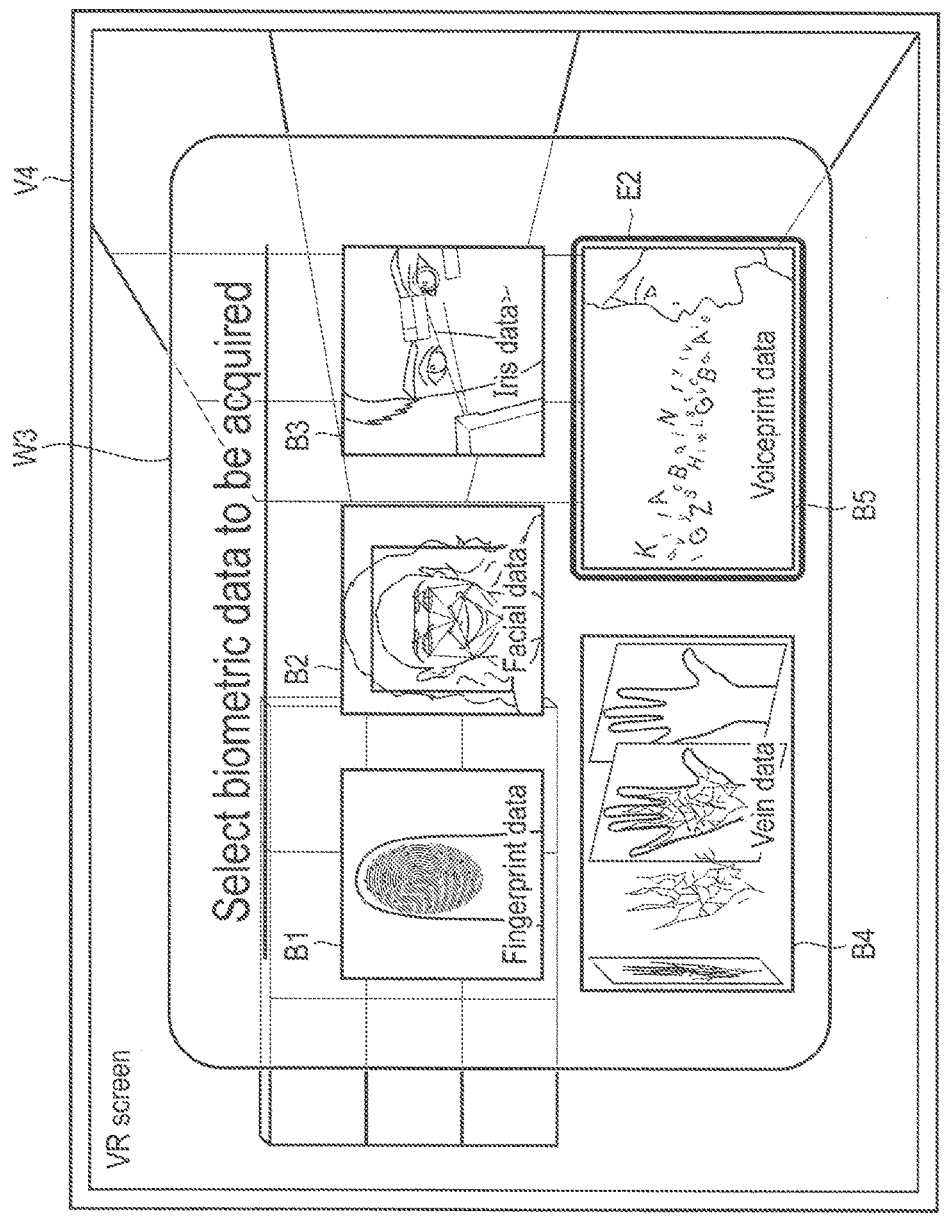
F I G. 13

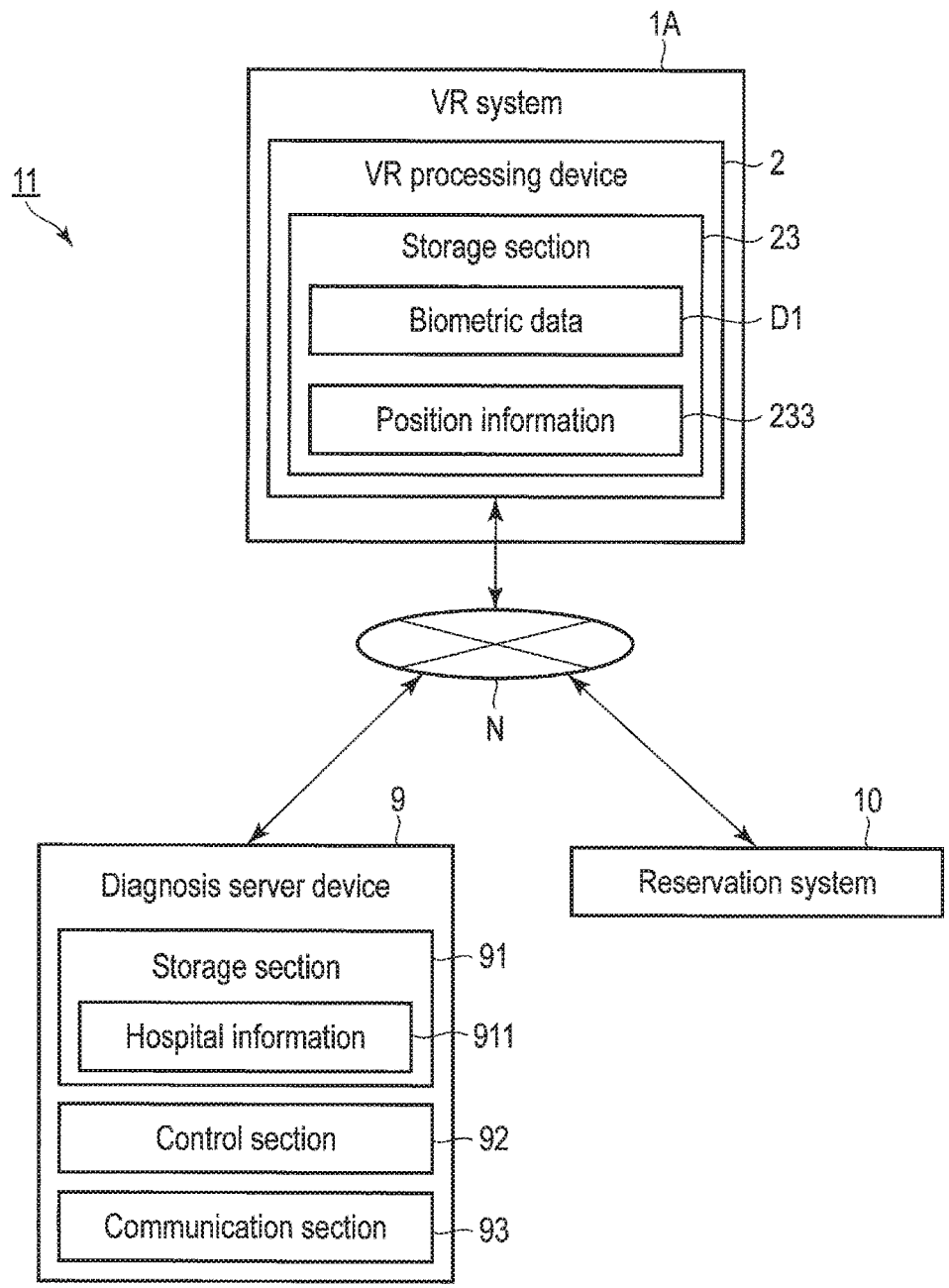
F I G. 17

VIRTUAL REALITY SYSTEM AND INFORMATION PROCESSING SYSTEM

CROSS-REFERENCE TO RELATED APPLICATIONS

This application is a Continuation Application of PCT Application No. PCT/JP2016/071046, filed Jul. 15, 2016, the entire contents of which are incorporated herein by reference.

BACKGROUND OF THE PRESENT DISCLOSURE

1. Field of the Present Disclosure

The present disclosure relates to a virtual reality system and information processing system.

2. Description of the Related Art

In recent years, development of systems associated with Virtual Reality (hereinafter abbreviated as VR) is ardently carried out. In general, when a user experiences the content of VR, the user wears a device (hereinafter referred to as a VR headset) having a goggles-like shape on his or her head. The VR headset is provided with two displays respectively corresponding to right and left eyes and, on each of the displays, an image having a parallax for the user watching the image to obtain a sense of depth (or sense of extrusion) is displayed.

Further, the VR headset incorporates therein a position sensor, acceleration sensor, gyroscopic sensor, and the like to change the image to be displayed on the display each time the position or direction of the head of the user changes as if the sight of the user were moved in the direction in which the position or direction of the head of the user has changed. Thereby, the user can obtain a sense of actually moving his or her head in the VR.

BRIEF SUMMARY OF THE PRESENT DISCLOSURE

1. Technical Problem

In general, for example, when it becomes necessary for a user to carry out payment processing for purchase or the like of the paid content provided in the VR, the user who experiences VR by using a VR headset needs to take off the VR headset and carry out an operation for payment. The operation for payment is, for example, inputting a card number of a credit card, inputting a personal identification number, inputting personal information, and the like. However, it is troublesome for the user to take off the VR headset from his or her head for each payment, and put the VR headset again on his or her head after the payment is finished and, furthermore taking off the VR headset deteriorates the sense of immersion of the user experiencing VR.

Further, in a game or the like in which a VR headset is utilized, it is conceivable that one VR headset and VR machine are shared among a plurality of persons, for example, a family or the like and, in this case, it is desirable that the security of payment be ensured.

The present disclosure has been contrived in consideration of these circumstances, and provides a VR system making it easy for the user who uses the VR headset to carry out payment, and ensuring the security of the payment.

2. Means of Solving the Technical Problem

According to one embodiment of the present disclosure, a virtual reality system includes a controller, a first information processing device, a virtual reality headset, a biometric data acquisition device, a first sensor, and a second sensor. The controller accepts an instruction from a user. The first information processing device creates virtual reality content according to an instruction received from the controller. The virtual reality headset is worn by the user and displays the virtual reality content received from the first information processing device to the user. The biometric data acquisition device acquires biometric data of the user. The first sensor creates first position information indicating a position of the biometric data acquisition device, and first direction information indicating a direction of the biometric data acquisition device, and transmits the first position information and the first direction information to the first information processing device. The second sensor configured to create second position information indicating a position of the virtual reality headset, and second direction information indicating a direction of the virtual reality headset, and transmit the second position information and the second direction information to the first information processing device. The second information processing device is connected to the first information processing device in such a manner that the second information processing device can communicate with the first information processing device. The first information processing device includes a content creation section, content transmission section, and biometric data transmission section. The content creation section, when a payment instruction is received from the controller, adds an image making the user wearing the virtual reality headset recognize the position and the direction of the biometric data acquisition device, and prompting the user wearing the virtual reality headset to input biometric data by means of the biometric data acquisition device to the virtual reality content on the basis of the first position information and the first direction information received from the first sensor, and the second position information and the second direction information received from the second sensor. The content transmission section transmits the virtual reality content to the virtual reality headset. The biometric data transmission section, after the virtual reality content including the image prompting the user to input the biometric data is displayed by the virtual reality headset, receives the biometric data of the user from the biometric data acquisition device, and transmits the biometric data to the second information processing device. The second information processing device includes a biometric authentication section configured to collate the biometric data received from the first information processing device, and already-registered biometric data of the user stored in a storage device referred to by the second information processing device with each other and, when the collation is successful, permit the payment instruction.

3. Advantage of the Present Disclosure

According to the present disclosure, it is possible to make it easy for the user who uses a VR headset to make his or her payment, and ensure the security of the payment.

Additional objects and advantages of the present disclosure will be set forth in the description which follows, and in part will be obvious from the description, or may be learned by practice of the present disclosure. The objects and advantages of the present disclosure may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the present disclosure, and together with the general description given above and the detailed description of the embodiments given below, serve to explain the principles of the present disclosure.

FIG. 9 is a flowchart exemplifying a biometric data collation processing according to the first embodiment.

FIG. 10 is a flowchart exemplifying a biometric data registration processing according to the first embodiment.

FIG. 11 is a view showing a first example of the VR screen display at the time of biometric data registration or at the time of biometric data acquisition according to the first embodiment.

FIG. 13 is a view exemplifying the VR screen display at the time of biometric data selection according to the first embodiment.

FIG. 17 is a block diagram exemplifying a configuration of an automatic diagnosis system according to a third embodiment.

DETAILED DESCRIPTION OF THE PRESENT DISCLOSURE

Hereinafter, embodiments of the present disclosure will be described with reference to the accompanying drawings. It should be noted that in the description to be given hereinafter, approximately or substantially identical functions and constituent elements are denoted by identical reference symbols, and descriptions are given only when necessary.

First Embodiment

In this embodiment, a VR system configured to detect a position and direction of a biometric data acquisition device included in the VR system, display an image enabling the user wearing a VR headset to recognize the position and direction of the biometric data acquisition device on each display of the VR headset, and thereby enable the user to input biometric data while wearing the VR headset as it is will be described below.

In this embodiment, the direction of the biometric data acquisition device implies a direction in which the biometric data acquisition device can acquire biometric data with high degrees of sensitivity and accuracy, in other words, the direction may be made a direction in which the biometric data acquisition device carries out sensing.

In this embodiment, identification information is called an ID.

In this embodiment, biometric data may be, for example, fingerprint data, vein data, artery data, palm pattern data, retina data, iris data, facial data, vascular data, voice data, voiceprint data, and auriculate data, and may be other data.

In this embodiment, the biometric data acquisition device may be made, for example, a biometric sensor, camera, microphone, and the like for acquiring the biometric data.

In this embodiment, a case where the payment to be made by the user is a card payment will be described. The type of the card may be, for example, a credit card, debit card, prepaid card, electronic money card, point card, and cash card or may be other types of cards for making an electronic payment. However, this embodiment is also applicable to a case where the medium or product used for the payment is not a card. The payment in this embodiment may be made a payment by a virtual currency.

In this embodiment, the content includes, for example, software including at least one of image data, video data, program, and data, and includes voice data and the like. The content may be, for example, a game program or the like.

Figure 1:
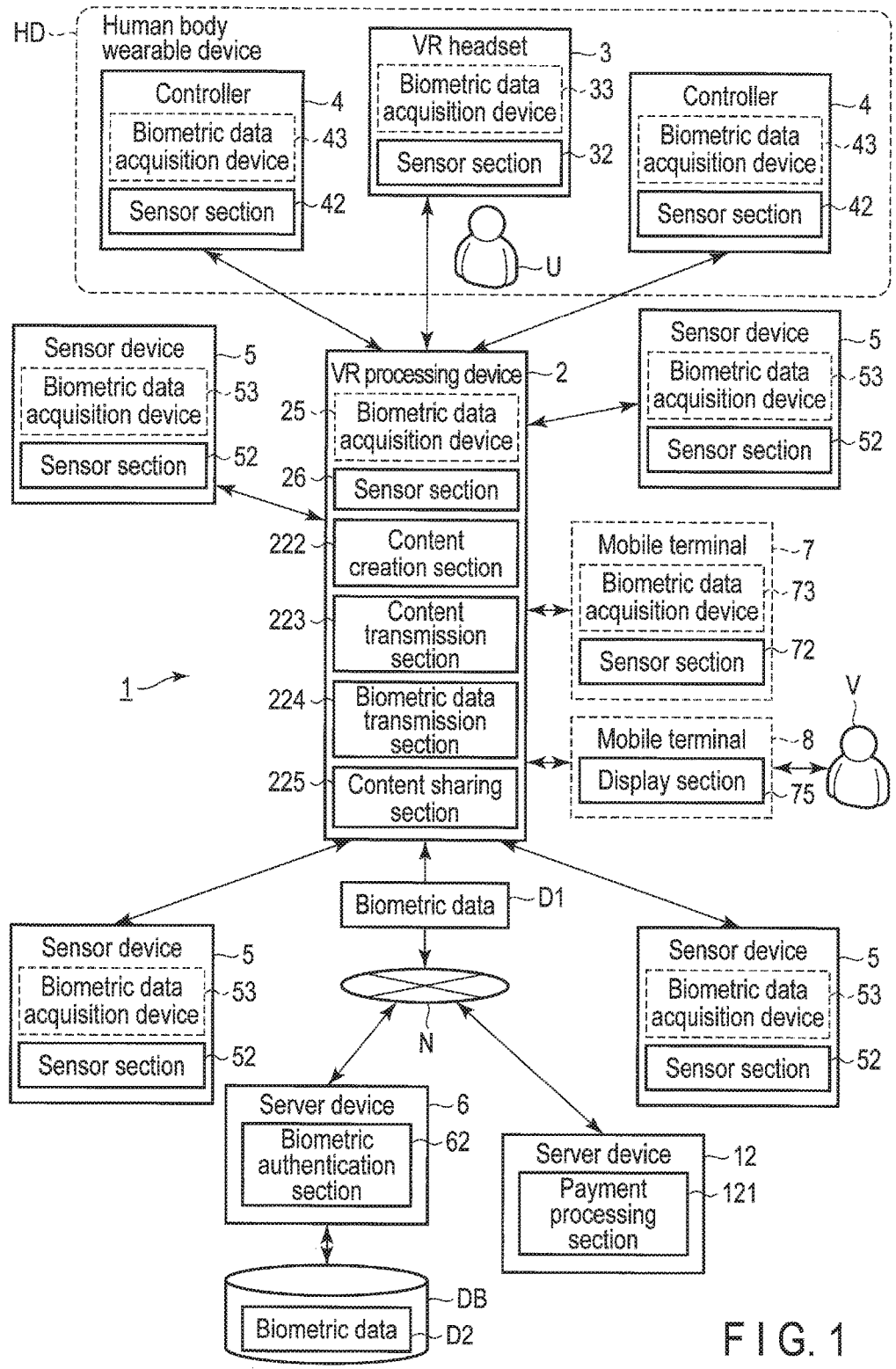
FIG. 1 is a block diagram showing a configuration example of a VR system according to a first embodiment.

FIG. 1 is a block diagram showing a configuration example of a VR system 1 according to this embodiment.

The VR system 1 includes a VR processing device 2, human body wearable device HD, sensor devices 5, and server devices 6 and 12. The human body wearable device HD includes a VR headset 3 and controllers 4. The VR headset 3 and controllers 4 are devices to be worn by the user U or directly held by the user with his or her hands. By the VR headset 3 and controllers 4, the VR system 1 can be controlled. Further, the VR system 1 may include a mobile terminal 7 of the user U, and may include a mobile terminal 8 of another user V other than the user U. The mobile terminals 7 and 8, and VR processing device 2 may be made able to communicate with each other through, for example, a network N or may be made able to communicate with each other not through the network N. More specifically, the mobile terminals 7 and 8, and VR processing device 2 may be made able to communicate with each other through, for example, a telephone line or the Internet. The mobile terminals 7 and 8, and VR processing device 2 may be made able to communicate with each other by, for example, wireless LAN communication, communicate with each other by Near Field Communication or communicate with each other by infrared communication.

The VR headset 3 is a device to be worn by the user U on his or her head. The VR headset 3 is provided with displays, and each display displays VR content created by the VR processing device 2. The user U visually confirms the VR content displayed on each display to thereby be able to experience VR.

The VR headset 3 includes, for example, a biometric data acquisition device 33 and sensor section 32.

The biometric data acquisition device 33 acquires biometric data of the user U by, for example, coming into contact with the user U or in a noncontact manner. More specifically, the biometric data acquisition device 33 includes biometric sensors corresponding to, for example, fingerprint data, vein data, artery data, palm pattern data, retina data, iris data or voiceprint data.

The sensor section 32 creates position information indicating the position of the VR headset 3 and direction information indicating the direction of the VR headset 3, and transmits the position information and direction information about the VR headset 3 to the VR processing device 2. Besides, the sensor section 32 corresponds to the biometric data acquisition device 33, and may be configured to create position information indicating the position of the biometric data acquisition device 33 and direction information indicating the direction of the biometric data acquisition device 33, and transmit the position information and direction information about the biometric data acquisition device 33 to the VR processing device 2.

The controllers 4 are devices to be used by the user U to operate the VR system 1, and accept an instruction from the user U. The controllers 4 may be held by the user U with his both right and left hands to be operated, and may be worn by the user U on his or her right and left legs or on other parts of the user U. In the following description, it is assumed that the number of controllers 4 included in the VR system 1 is two, and each of the controllers 4 is held by the right or left hand of the user U to be operated.

The controller 4 includes a biometric data acquisition device 43 and sensor section 42.

The biometric data acquisition device 43 acquires biometric data of the user U by, for example, coming into contact with the user U or in a noncontact manner. More specifically, the biometric data acquisition device 43 includes biometric sensors corresponding to, for example, fingerprint data, vein data, artery data, palm pattern data or voiceprint data.

The sensor section 42 creates position information indicating the position of the controller 4 and direction information indicating the direction of the controller 4, and transmits the position information and direction information about the controller 4 to the VR processing device 2. Besides, the sensor section 42 corresponds to the biometric data acquisition device 43, and creates position information indicating the position of the biometric data acquisition device 43 and direction information indicating the direction of the biometric data acquisition device 43, and transmits the position information and direction information about the biometric data acquisition device 43 to the VR processing device 2.

The sensor device 5 is a device configured to assist the construction of VR to be experienced by the user U. More specifically, for example, when the plurality of sensor devices 5 are connected to the VR processing device 2, the VR processing device 2 may display the each position of the sensor devices 5 on each display with which the VR headset 3 is provided to thereby indicate the range within which the user U wearing the VR headset 3 can move. Further, for example, the VR processing device 2 may use the sensors provided in the plurality of sensor devices 5 to measure the movement, posture, specific position of the body, and the like of the user U. Further, for example, the sensor device 5 may make a sound when the user U gets closer thereto to thereby give a sense of realism to the user. In the following description, it is assumed that the number of the sensor devices 5 included in the VR system 1 is four.

The sensor device 5 includes a biometric data acquisition device 53 and sensor section 52.

The biometric data acquisition device 53 acquires biometric data of the user U, for example, without coming into contact with the user U. More specifically, the biometric data acquisition device 53 includes, for example, a biometric sensor corresponding to voiceprint data and camera.

The sensor section 52 creates position information indicating the position of the sensor device 5 and direction information indicating the direction of the sensor device 5, and transmits the position information and direction information about the sensor device 5 to the VR processing device 2. Besides, the sensor section 52 corresponds to the biometric data acquisition device 53, and creates position information indicating the position of the biometric data acquisition device 53 and direction information indicating the direction of the biometric data acquisition device 53, and transmits the position information and direction information about the biometric data acquisition device 53 to the VR processing device 2.

The mobile terminal 7 can communicate with the VR processing device 2. The mobile terminal 7 may be, for example, a mobile telephone such as a smartphone, tablet terminal or the like.

The mobile terminal 7 may be used in place of the controller 4. That is, the user U may be made possible to operate the VR system 1 by using the mobile terminal 7. The mobile terminal 7 includes, for example, a biometric data acquisition device 73 and sensor section 72, and may be utilized to input biometric data of the user U.

The biometric data acquisition device 73 acquires biometric data of the user U by, for example, coming into contact with the user U or in a noncontact manner. More specifically, the biometric data acquisition device 73 includes biometric sensors corresponding to, for example, fingerprint data, vein data, artery data, palm pattern data or voiceprint data.

The sensor section 72 creates position information indicating the position of the mobile terminal 7 and direction information indicating the direction of the mobile terminal 7, and transmits the position information and direction information about the mobile terminal 7 to the VR processing device 2. Besides, the sensor section 72 corresponds to the biometric data acquisition device 73, creates position information indicating the position of the biometric data acquisition device 73 and direction information indicating the direction of the biometric data acquisition device 73, and transmits the position information and direction information about the biometric data acquisition device 73 to the VR processing device 2.

The VR processing device 2 carries out control of the whole VR system 1 or a calculation necessary for the control. The VR processing device 2 can communicate with the VR headset 3, at least one or more controllers 4, and at least one or more sensor devices 5 by cable or by wireless.

The VR processing device 2 creates VR content according to an instruction received from the controller 4. The VR processing device 2 includes, for example, a biometric data acquisition device 25, sensor section 26, content creation section 222, content transmission section 223, biometric data transmission section 224, and content sharing section 225.

The biometric data acquisition device 25 acquires biometric data of the user U by, for example, coming into contact with the user U or in a noncontact manner. More specifically, the biometric data acquisition device 25 includes biometric sensors corresponding to, for example, fingerprint data, vein data, artery data, palm pattern data or voiceprint data.

The sensor section 26 corresponds to the biometric data acquisition device 25, and creates position information indicating the position of the biometric data acquisition device 25 and direction information indicating the direction of the biometric data acquisition device 25. Besides, the sensor section 26 may be configured to create position information indicating the position of the VR headset 3 and direction information indicating the direction of the VR headset 3 by, for example, detecting light of a light mounted on the VR headset 3, or the like.

Upon receipt of a payment instruction from the controller 4, the content creation section 222 adds an image making the user U wearing the VR headset 3 recognize the positions and directions of the biometric data acquisition devices 25, 33, 43, 53, and 73 on the basis of position information items and direction information items about the biometric data acquisition devices 25, 33, 43, 53, and 73 received from the sensor sections 26, 32, 42, 52, and 72, and position information items and direction information items about the user U received from the sensor sections 26, 32, and 52, and prompting the user U wearing the VR headset 3 to input biometric data by means of the biometric data acquisition devices 25, 33, 43, 53, and 73 to the VR content.

The content transmission section 223 transmits VR content to the VR headset 3.

After the VR content including the image prompting the user U to input biometric data is displayed by the VR headset 3, the biometric data transmission section 224 receives biometric data D1 of the user U from one of the biometric data acquisition devices 25, 33, 43, 53, and 73, and transmits the biometric data D1 to the server device 6.

The content sharing section 225 enables the VR content displayed on a display section 37 of the VR headset to be displayed also on the mobile terminal 8 operated by another user V who is not the user U. That is, the content sharing section 225 carries out authentication of the mobile terminal 8 which can communicate with the VR processing device 2 and, when the authentication of the mobile terminal 8 is successful, permits communication between the VR processing device 2 and mobile terminal 8, converts the VR content into content suited to the mobile terminal 8, and transmits the converted content to the mobile terminal 8. For example, the user V is a friend or the family or the like of the user U. For example, the content transmitted to the mobile terminal 8 may be content formed by converting the VR content into content not suited to the VR or may be content formed by converting the VR content into content suited to the browser of the mobile terminal 8.

The mobile terminal 8 is provided with a display section 75, and displays the content received from the content sharing section 225.

The server device 6 is connected to the VR processing device 2 through the network N in such a manner the server device 6 can communicate with the VR processing device 2. The server device 6 can refer to a database DB. The database DB stores therein already-registered biometric data D2 of the user U.

The server device 6 includes a biometric authentication section 62. The biometric authentication section 62 collates biometric data D1 received from the VR processing device 2 through the network N and already-registered biometric data D2 stored in the database DB with each other. When the collation is successful, the server device 6 transmits a payment permission notification indicating that a payment is permitted to the server device 12 through the network N.

The server device 12 is connected to the VR processing device 2 and server device 6 through the network in such a manner that the server device 12 can communicate with the VR processing device 2 and server device 6. This server device 12 may be integrated with the server device 6. The server device 12 includes a payment processing section 121. Upon receipt of a payment permission notification from the server device 6 through the network N, the payment processing section 121 executes payment processing for the user U according to the payment instruction received from the VR processing device 2 through the network N.

In this embodiment, the server device 12 is, for example, a server device of the acquirer (card clearance company), or a server device of the issuer (card issuance company) or a card brand.

It should be noticed that in this embodiment, when the content sharing section 225 is transmitting content to the mobile terminal 8, the content creation section 222 adds an image or characters indicating that the content is shared to the VR content. The content transmission section 223 transmits VR content including the image or characters indicating that the content is shared to the VR head set 3. Thereby, the user U wearing the VR headset 3 can recognize that the user V shares the content.

Further, the content creation section 222 may add, on the basis of a difference between the position information about any one of the biometric data acquisition devices and position information about the VR headset 3, and a difference between the direction information about any one of the biometric data acquisition devices and direction information about the VR headset 3, an image for guiding the user U to any one of the biometric data acquisition devices to the VR content.

Furthermore, the content creation section 222 may determine, on the basis of the biometric data D1 acquired by any one of the biometric data acquisition devices, the attribute of a character corresponding to the user U, and create VR content according to the attribute. The content creation section 222 may receive the biometric data D2 stored in the database DB through the server device 6 and network N, determine the attribute of the character corresponding to the user U on the basis of the received biometric data D2, and create VR content according to the attribute.

Figure 2:
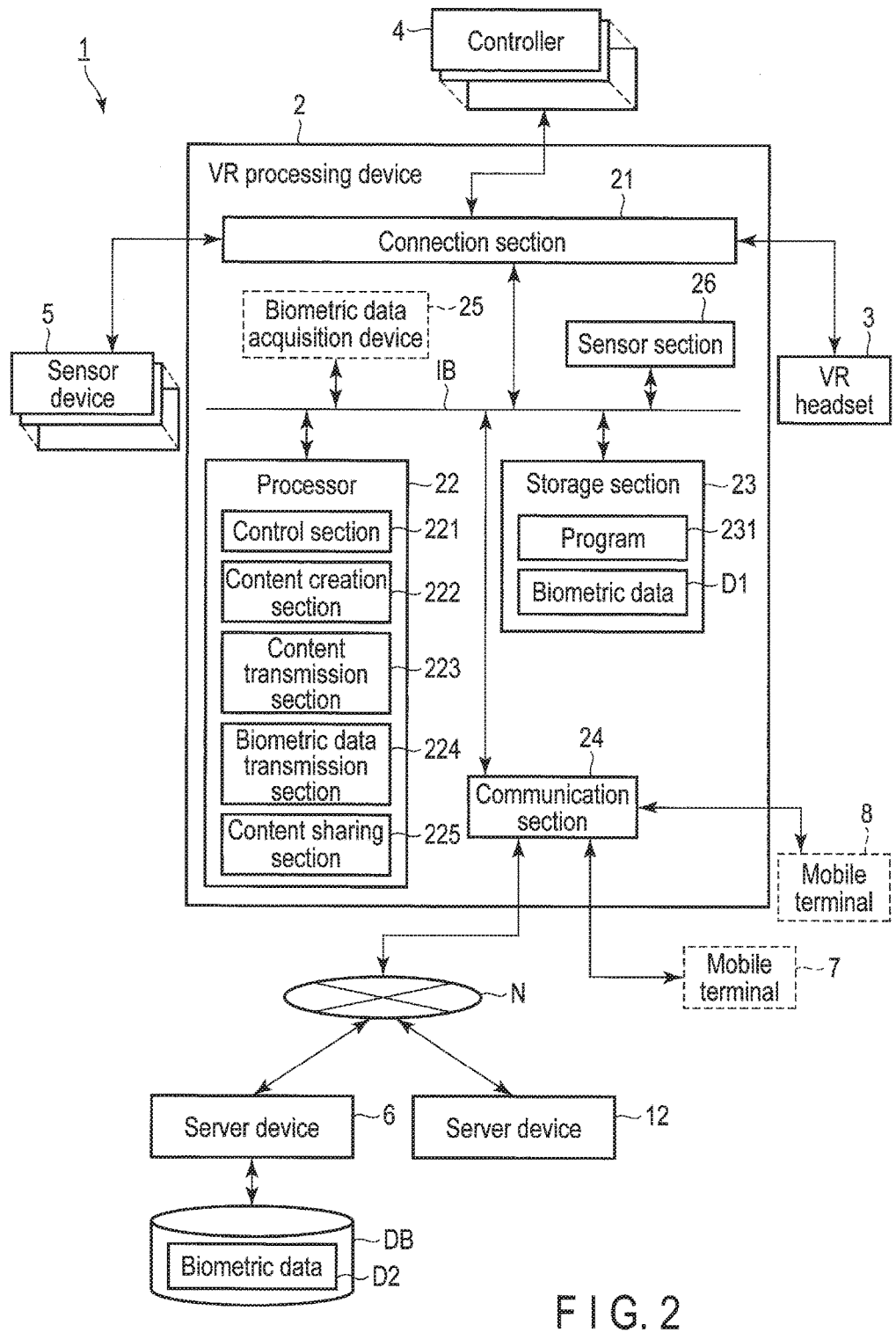
FIG. 2 is a block diagram showing a configuration example of a VR processing device 2 according to the first embodiment.

FIG. 2 is a block diagram showing a configuration example of the VR processing device 2 according to this embodiment.

The VR processing device 2 includes a connection section 21, processor 22, storage section 23, communication section 24, biometric data acquisition device 25, and sensor section 26. The VR processing device 2 may not include the biometric data acquisition device 25. The above-mentioned processing sections can communicate with each other through an internal bus IB.

It should be noted that the descriptions of the processing sections already given in connection with FIG. 1 are omitted.

The connection section 21 connects the VR processing device 2 to the VR headset 3, controllers 4, and sensor devices 5.

The processor 22 carries out calculation processing of the VR system 1. The processor 22 includes control section 221, the content creation section 222, content transmission section 223, biometric data transmission section 224, and content sharing section 225.

The processor 22 may be, for example, a Central Processing Unit (CPU), Micro-Processing Unit (MPU), Digital Signal Processor (DSP) or the like.

The control section 221 carries out control of the whole VR system 1. The control section 221 transmits/receives commands, addresses, data items, information items, instructions, signals, and the like to/from the VR headset 3, controllers 4, and sensor devices 5 through the connection section 21.

The content creation section 222 creates VR content to be displayed on each display provided in the VR headset 3. The VR content created by the content creation section 222 is transmitted by the content transmission section 223 to the VR headset 3 through the connection section 21. Further, the VR content may also be transmitted to the external devices such as the mobile terminals 7 and 8 through the communication section 24.

The storage section 23 may be used as, for example, a main storage device. The storage section 23 follows the control from the processor 22. In the storage section 23, data or the like processed by the processor 22 is temporarily stored on the basis of the control of the processor 22.

The storage section 23 stores a program 231 in, for example, a nonvolatile storage area. The processor 22 may be configured to execute the program 231 to thereby realize the functions as the control section 221, content creation section 222, content transmission section 223, biometric data transmission section 224, and content sharing section 225.

The storage section 23 stores therein the biometric data D1. The biometric data D1 is the biometric data of the user U acquired by using one of the biometric data acquisition devices 25, 33, 43, 53, and 73.

The communication section 24 transmits/receives commands, addresses, data items, information items, instructions, signals, and the like to/from, for example, the VR processing device 2, server devices 6 and 12, and mobile terminals 7 and 8 through the network N. It should be noted that the communication section 24 may carry out communication with devices other than the server devices 6 and 12, and mobile terminals 7 and 8 through the network N.

It should be noted that the VR processing device 2 may be, for example, a general-purpose personal computer (PC) or may be hardware for the exclusive use of the VR system 1.

Figure 3:
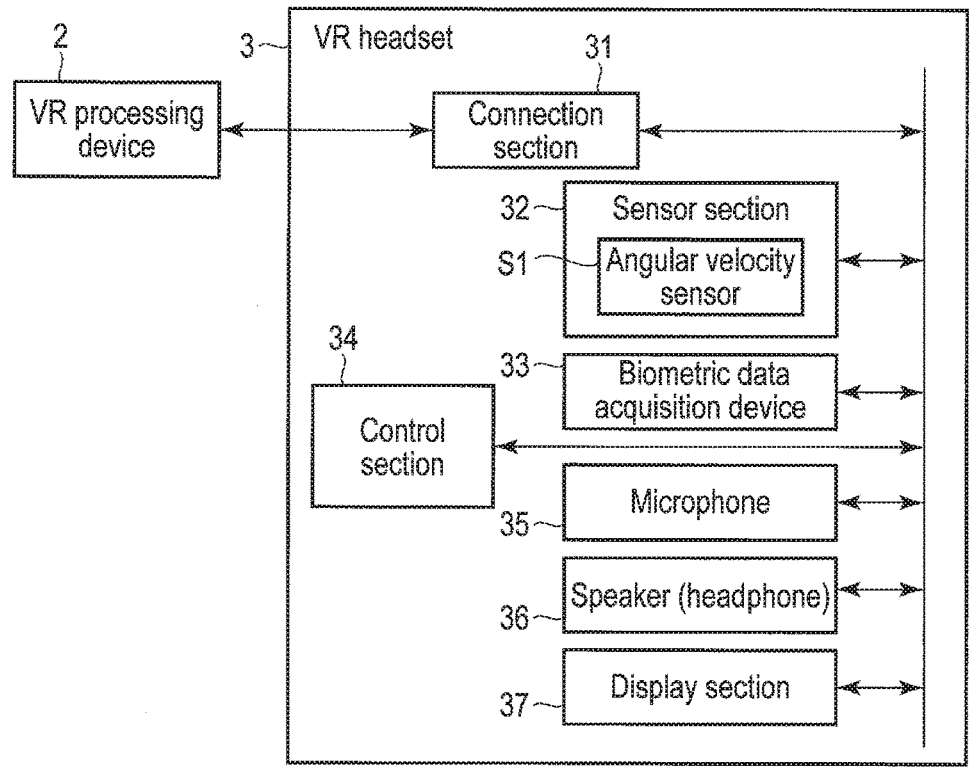
FIG. 3 is a block diagram showing a configuration example of a VR headset according to the first embodiment.

FIG. 3 is a block diagram showing a configuration example of the VR headset 3 according to this embodiment.

The VR headset 3 includes a connection section 31, sensor section 32, biometric data acquisition device 33, control section 34, microphone 35, speaker 36, and display section 37.

It should be noted that descriptions of processing sections already described in connection with FIG. 1 are omitted.

The connection section 31 connects the VR headset 3 and VR processing device 2 to each other.

The sensor section 32 includes an angular velocity sensor (gyroscopic sensor) S1. The sensor section 32 may be incorporated in the biometric data acquisition device 33 or may be provided in the vicinity of the biometric data acquisition device 33.

The angular velocity sensor S1 is a sensor capable of detecting a rotational angle and change in direction of a substance provided with a sensor. That is, by virtue of the angular velocity sensor S1, a change in position and direction of the VR headset can be detected.

It should be noted that the sensor included in the sensor section 32 is not limited to that described above and, for example, a proximity sensor, acceleration sensor, position sensor, magnetic sensor, luminance sensor, and the like may also be included.

The control section 34 carries out control of the processing sections included in the VR headset 3. The control section transmits/receives commands, addresses, data items, information items, instructions, signals, and the like to/from the VR processing device 2 through the connection section 31. More specifically, for example, the control section 34 transmits sensor data such as position information and direction information acquired by the sensor section 32, biometric data acquired by the biometric data acquisition device 33, and voice data input to the microphone 35 to the VR processing device 2 through the connection section 31. Further, for example, the control section 34 receives voice data from the VR processing device 2 through the connection section 31, and outputs the voice data to the speaker 36, and receives VR content, and outputs the VR content to the display section 37.

The microphone 35 inputs the voice of the user U to the VR system 1. It should be noted that when the VR headset 3 can acquire biometric data of a voiceprint, the microphone 35 may also serve as the biometric data acquisition device 33.

The speaker 36 outputs a sound created by the VR processing device 2 or sound created by the control section 34. The speaker 36 may be, for example, headphones.

The display section 37 displays the VR content created by the content creation section 222 of the VR processing device 2. The display section 37 is provided with two displays corresponding to the both eyes of the user U. In the following descriptions, the display section 37 in a state where VR content is displayed is referred to as a VR screen.

Figure 4:
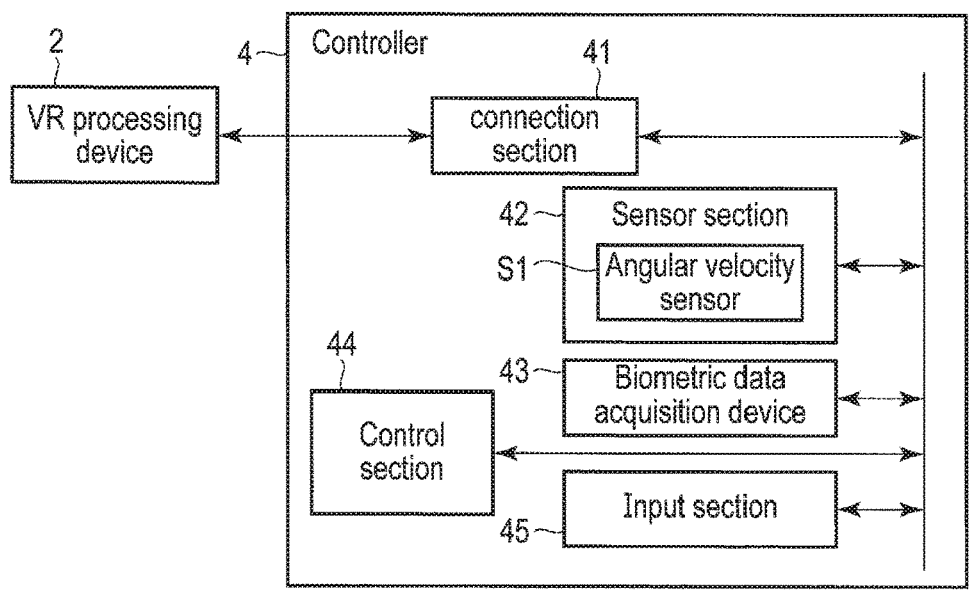
FIG. 4 is a block diagram showing a configuration example of a controller according to the first embodiment.

FIG. 4 is a block diagram showing a configuration example of the controller 4 according to this embodiment.

The controller 4 includes a connection section 41, sensor section 42, biometric data acquisition device 43, control section 44, and input section 45.

It should be noted that descriptions of processing sections already described in connection with FIG. 1 are omitted.

The connection section 41 connects the controller 4 and VR processing device 2 to each other.

The configuration of the sensor section 42 is equivalent to the sensor section 32.

The control section 44 carries out control of the processing sections included in the controller 4. The control section 44 transmits/receives commands, addresses, data items, information items, instructions, signals, and the like to/from the VR processing device 2 through the connection section 41. More specifically, for example, the control section 44 transmits sensor data such as position information and direction information acquired by the sensor section 42, biometric data acquired by the biometric data acquisition device 43, and data input to the input section 45 to the VR processing device 2 through the connection section 41.

The input section 45 accepts an operation of the user U. The input section 45 may be, for example, a button, analog stick, rotary encoder, touch panel, various types of sensors, and the like.

Figure 5:
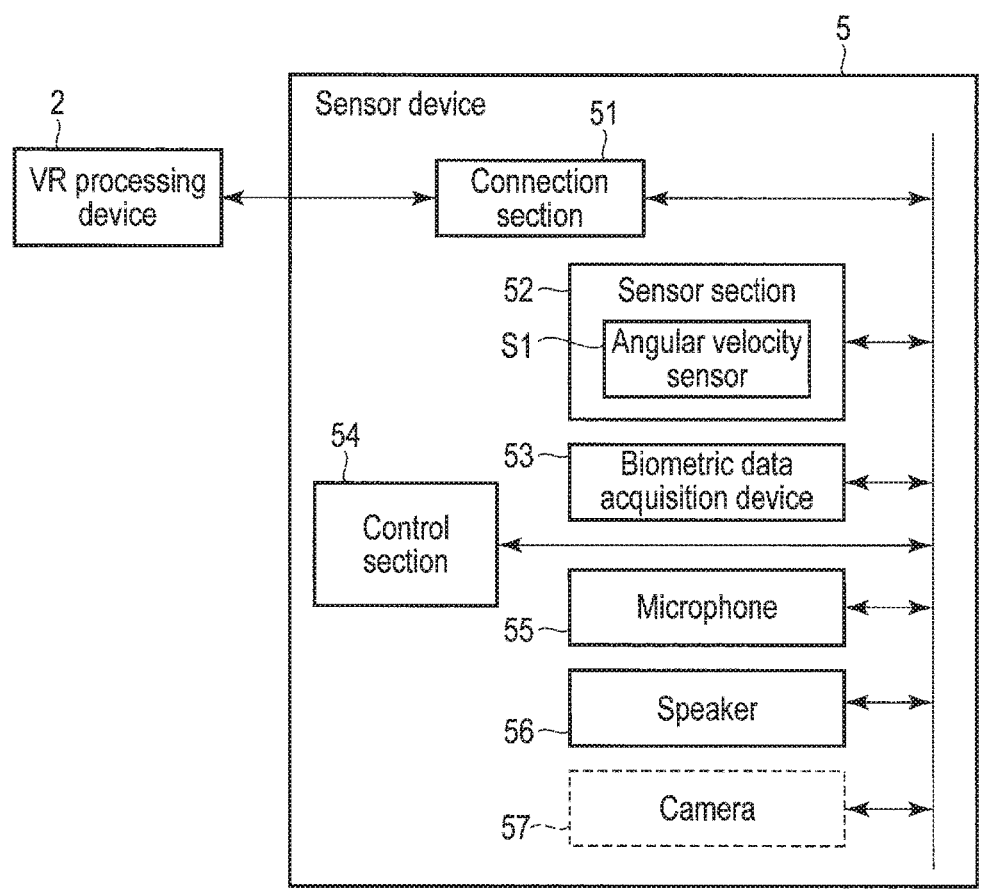
FIG. 5 is a block diagram showing a configuration example of a sensor device according to the first embodiment.

FIG. 5 is a block diagram showing a configuration example of the sensor device 5 according to this embodiment.

The sensor device 5 includes a connection section 51, sensor section 52, biometric data acquisition device 53, control section 54, microphone 55, and speaker 56. Further, the sensor device 5 may also include a camera.

It should be noticed that descriptions of processing sections already described in connection with FIG. 1 are omitted.

The connection section 51 connects the sensor device 5 and VR processing device 2 to each other.

The configuration of the sensor section 52 is identical to the sensor section 32.

The control section 54 carries out control of the processing sections included in the sensor device 5. The control section 54 transmits/receives commands, addresses, data items, information items, instructions, signals, and the like to/from the VR processing device 2 through the connection section 51. The operation of the control section 54 is equivalent to the operations of the control sections 34 and 44.

The microphone 55 inputs the voice of the user U to the VR system 1. It should be noted that when the sensor device 5 can acquire biometric data of a voiceprint, the microphone 55 may also serve as the biometric data acquisition device 53.

The speaker 56 outputs a sound created by the VR processing device 2 or sound created by the control section 54.

The camera 57 shoots a still image or moving images. The camera 57 may be a camera capable of shooting a two-dimensional image or may be, for example, a stereo camera, infrared camera or the like capable of acquiring depth information. The control section 54 may be configured to subject the still image or moving images shot by the camera 57 to image processing to thereby enable, for example, a gesture of the user U or movement of a specific part of the user U such as his or her leg, arm, joint, and the like which cannot be recognized by the sensor section 52 or an object existing in the space within which the user U can move about to be recognized.

Figure 6:
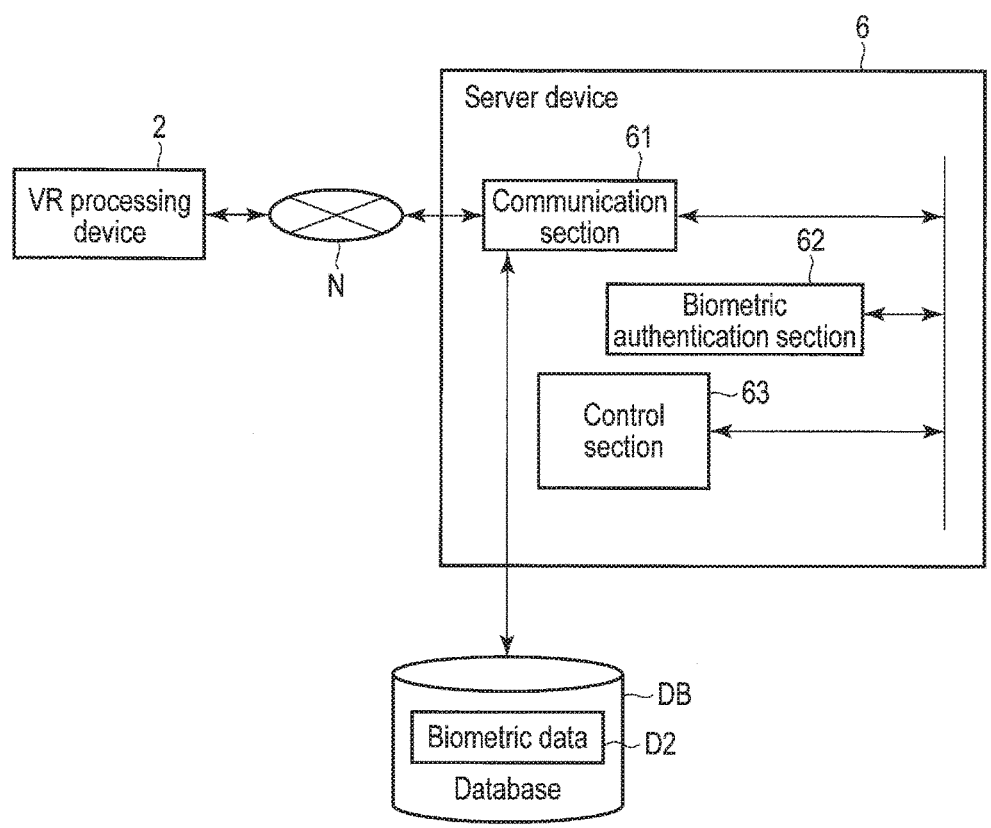
FIG. 6 is a block diagram showing a configuration example of a server device according to the first embodiment.

FIG. 6 is a block diagram showing a configuration example of the server device 6 according to this embodiment.

The server device 6 includes a communication section 61, biometric authentication section 62, and control section 63.

It should be noted that descriptions of the processing sections already described in connection with FIG. 1 are omitted.

The communication section 61 can be connected to the network N, and carries out communication with the VR processing device 2 through the network N. The communication section 61 can communicate with the database DB.

It should be noted that the database DB may be connected to the network N, and may be able to communicate with the server device 6 through the network N.

The control section 63 carries out control of the processing sections included in the server device 6. The control section 63 transmits/receives commands, addresses, data items, information items, instructions, signals, and the like to/from the VR processing device 2 and database DB through the communication section 61. For example, when the biometric authentication executed by the biometric authentication section 62 is successful, the control section 63 transmits a payment permission notification indicating that a payment is permitted to the server device 12 through the network N.

Figure 7:
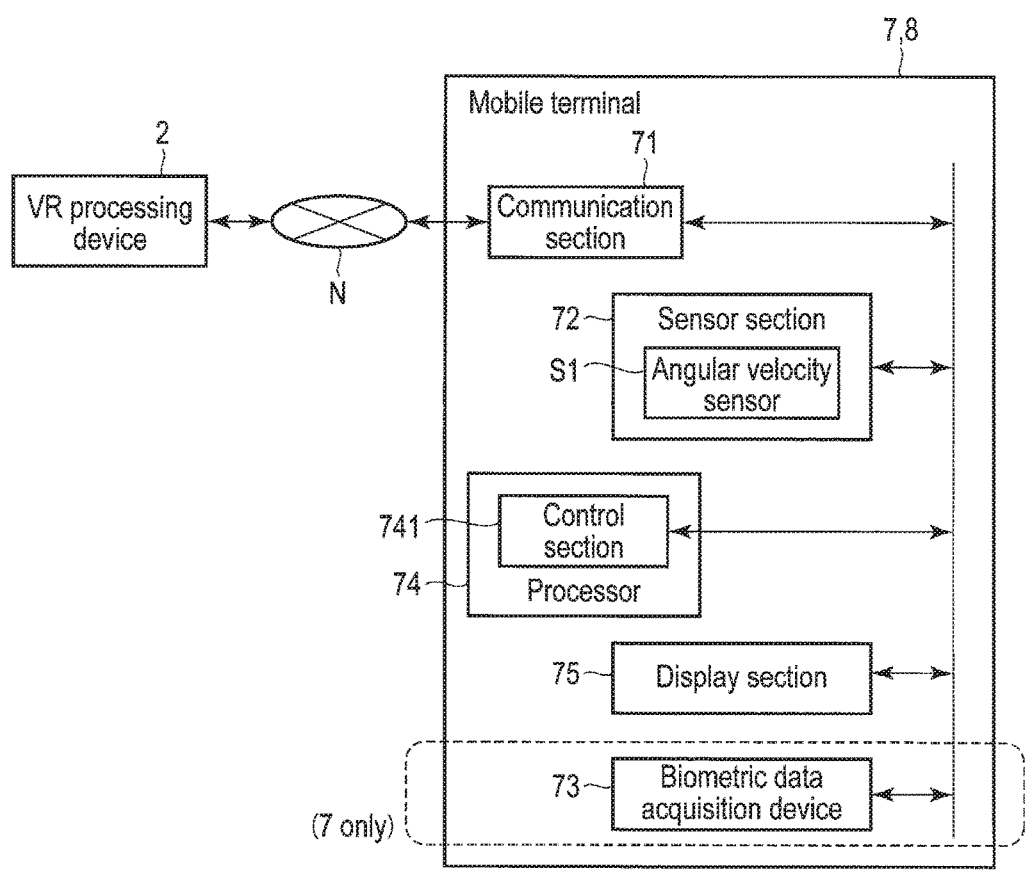
FIG. 7 is a block diagram showing a configuration example of mobile terminals according to the first embodiment.

FIG. 7 is a block diagram showing a configuration example of the mobile terminals 7 and 8 according to this embodiment.

The mobile terminal 7 includes a communication section 71, sensor section 72, biometric data acquisition device 73, processor 74, and display section 75.

The mobile terminal 8 includes a communication section 71, sensor section 72, processor 74, display section 75, and content sharing section 76. It should be noted that the mobile terminal 8 may be provided with a biometric data acquisition device 73.

It should be noted that descriptions of the processing sections already described in connection with FIG. 1 are omitted.

The communication section 71 can be connected to the network N, and carries out communication with the VR processing device 2 through the network N. The communication section 71 may be made able to directly communicate with the communication section 24 of the VR processing device 2 by cable or by wireless not through the network N.

The sensor section 72 is identical to the sensor section 32.

The processor 74 carries out calculation processing of the mobile terminal 7. The processor 74 includes a control section 741.

The control section 741 carries out control of the processing sections included in the mobile terminal 7. The control section 741 transmits/receives commands, addresses, data items, information items, instructions, signals, and the like to/from the VR processing device 2 through the communication section 71. The operation of the control section 741 is equivalent to those of the control sections 34, 44, and 54.

The display section 75 is, for example, a display of a general mobile terminal.

Further, as described above, when VR content is displayed on the display section 75 of the mobile terminal 8 by the content sharing section 225, it is desirable that the mobile terminal 8 be authenticated (login) by the VR system 1. When login to the VR system 1 is carried out, for example, a login ID and password may be used. More specifically, for example, when the mobile terminal 8 accesses the VR processing device 2, the VR processing device 2 displays a login screen on the display section 75 or display section 37 of the VR headset 3. The user U inputs a login ID and password according to the instruction of the login screen.

It should be noticed that when the mobile terminal 8 is provided with the biometric data acquisition device 73, biometric authentication may be used for login to the VR system 1. In this case, the procedure for the biometric authentication is equivalent to the procedure (to be described later by using FIG. 9) for the biometric authentication to be carried out at the time of payment processing.

Figure 8:
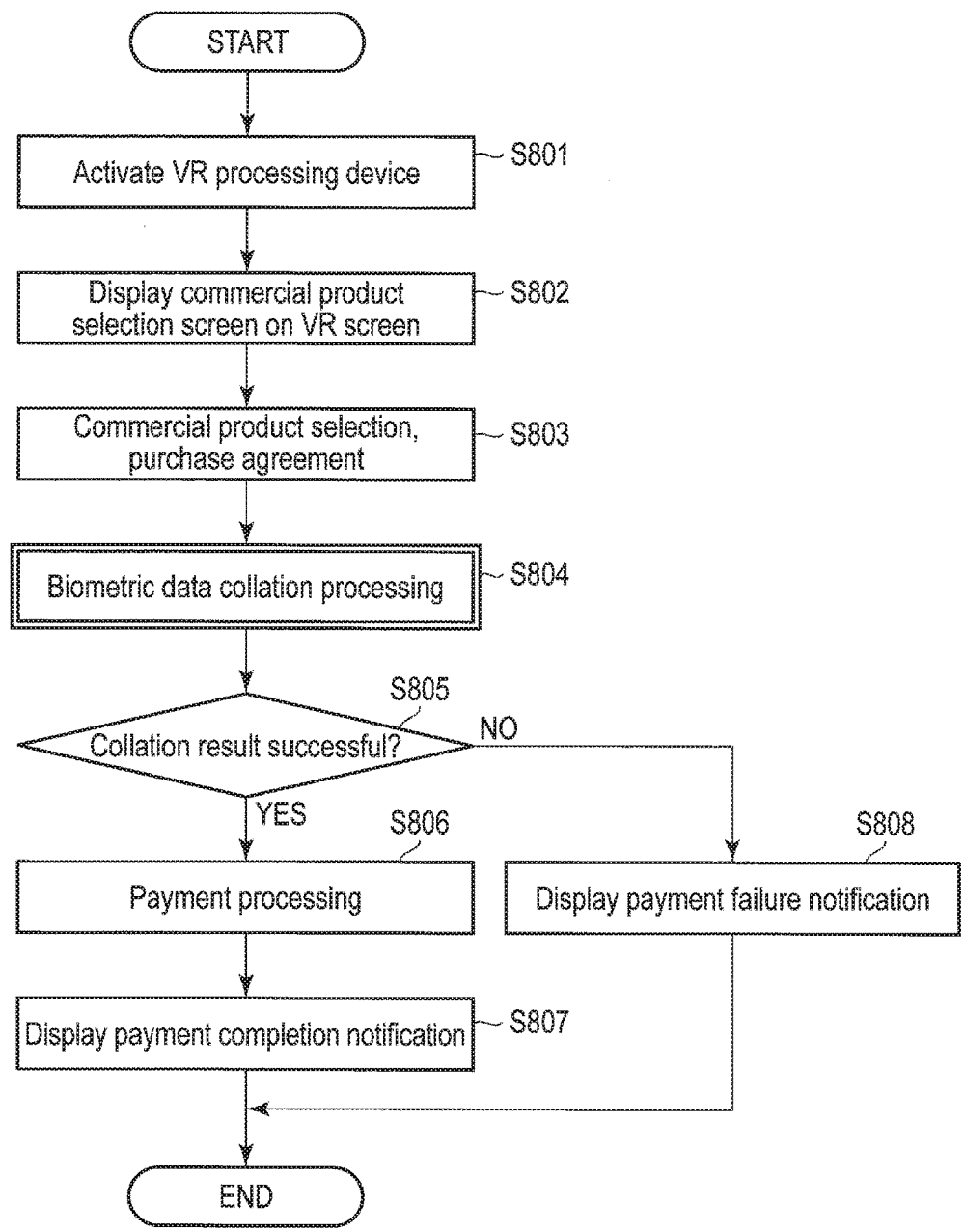
FIG. 8 is a flowchart exemplifying a payment processing using the VR system according to the first embodiment.

FIG. 8 is a flowchart exemplifying the payment processing using the VR system 1 according to this embodiment.

In step S801, the VR processing device 2 is activated. Power is also supplied to the VR headset 3, controllers 4, and sensor devices 5 which are connected to the VR processing device 2, and the devices become in a state in which they can be operated by the user U.

In step S802, VR content created by the content creation section 222 of the VR processing device 2 is transmitted to the VR headset 3 through the connection section 21. The display section 37 of the VR headset 3 displays the VR content received from the VR processing device 2. Furthermore, the content creation section 222 creates, according to the selection of the user or automatically, VR content which lets the user to select a commercial product and purchase it.

In step S803, on the commercial product selection screen displayed on the display section 37, a commercial product to be purchased by the user U is selected. The commercial product may be selected, for example, by the user U by operating the controller 4. Furthermore, when the purchase of the selected commercial product is agreed, the VR processing device 2 begins payment processing. Agreement of the purchase of the commercial product may be carried out by, for example, the user U by selecting the purchase button displayed in the VR content.

In step S804, the VR processing device 2 starts collation processing of the biometric data. Details of the biometric data collation processing will be described later in connection with FIG. 9.

In step S805, the VR processing device 2 confirms a result of the biometric data collation processing obtained by the processing of step S804.

When the biometric data collation processing result is successful, the VR processing device 2 or server device 6 transmits a payment permission notification to the server device 12. In this case, in step S806, the server device 12 receives the payment permission notification from the VR processing device 2, and the payment processing section 121 carries out payment processing. When the payment processing is completed, the server device 6 transmits a payment completion notification to the VR processing device 2 through the communication section 61. Furthermore, in step S807, the VR processing device 2 receives the payment completion notification, and the content creation section 222 creates VR content including an indication that the payment is completed.

Further, when the biometric data collation processing result is unsuccessful, the VR processing device 2 stops the payment processing. In this case, in step S808, the content creation section 222 of the VR processing device 2 creates VR content including an indication that the payment is unsuccessful.

It should be noted that the indication that the payment is completed or the payment is unsuccessful may also be, display based on a message, icon, dialog box or the like.

In this embodiment, the VR processing device 2 may carry out authentication (login) of the user U at the time of activation in step S801. For login to the VR system 1, biometric authentication may also be used. In this case, the procedure for the biometric authentication is equivalent to the procedure (see FIG. 9) for the biometric authentication to be carried out at the time of the payment processing.

FIG. 9 is a flowchart exemplifying the biometric data collation processing according to this embodiment.

In step S901, when a plurality of biometric data acquisition devices available in the VR system 1 exist, the VR processing device 2 makes the user U determine which biometric data acquisition device should be selected to acquire biometric data. When the user has specified a biometric data acquisition device, the processing is advanced to step S902.

When only one available biometric data acquisition device exists in the VR system 1 or when the VR processing device 2 does not make the user select a biometric data acquisition device, the processing is advanced to step S905.

In step S902, the VR processing device 2 detects position information and direction information about the biometric data acquisition device specified by the user U in step S901. More specifically, when the biometric data acquisition device 33 is specified, the VR processing device 2 receives position information and direction information about each of the VR headset 3 and biometric data acquisition device 33 detected by the sensor section 32 from the control section 34 of the VR headset 3. Likewise, when the biometric data acquisition device 43 is specified, the VR processing device 2 receives position information and direction information about each of the controller 4 and biometric data acquisition device 43 detected by the sensor section 42 from the control section 44. Alternatively, likewise, when the biometric data acquisition device 53 is specified, the VR processing device 2 receives position information and direction information about each of the sensor device 5 and biometric data acquisition device 53 detected by the sensor section 52 from the control section 54. Alternatively, likewise, when the biometric data acquisition device 73 is specified, the VR processing device 2 receives position information and direction information about the mobile terminal 7 and biometric data acquisition device 73 from the control section 741. The VR processing device 2 temporarily stores the received position information and direction information in the storage section 23.

In step S903, the VR processing device 2 displays the position information and direction information about each device detected in step S902 on the VR screen. More specifically, the content creation section 222 of the VR processing device 2 reads the position information and direction information about each device stored in step S902 from the storage section 23. The content creation section 222 superimposes an image of each device based on the read position information and direction information about each of the devices upon the original VR content to thereby create new VR content. An example of the VR content created by the above-mentioned processing will be described later in connection with FIG. 11.

In step S904, the VR processing device 2 makes the user U input biometric data to the specified biometric data acquisition device.

In step S905, the VR processing device 2 retrieves an available biometric data acquisition device. More specifically, the VR processing device 2 asks the VR headset 3, controllers 4, sensor devices 5, and mobile terminal 7 whether or not the biometric data acquisition devices 33, 43, 53, and 73 provided in the above devices are available.

The control sections 34, 44, 54, and 74 confirm the states of the biometric data acquisition devices 33, 43, 53, and 73, and respectively transmit information indicating whether or not the biometric data acquisition devices are available to the VR processing device 2.

In step S906, the VR processing device 2 displays a position, direction, and type of each of the available biometric data acquisition devices obtained in step S905. The detection method and display method of the position and direction of the biometric data acquisition device are identical to the methods described in step S902 and step S903.

In step S907, the VR processing device 2 makes the user U input biometric data to any one of the biometric data acquisition devices displayed in step S906. In this case, for example, when the input of the biometric data by the user U is completed, each of the biometric data acquisition devices transmits biometric data D1 to the VR processing device 2. The VR processing device 2 receives the biometric data D1, and stores the biometric data D1 in the storage section 23.

It should be noticed that when biometric data items are received from a plurality of biometric data acquisition devices, the VR processing device 2 may store the received plurality of biometric data items in the storage section 23 and may store the firstly or lastly received biometric data in the storage section 23 as valid data.

In step S908, the VR processing device 2 transmits a biometric data collation instruction to the server device 6. More specifically, the biometric data transmission section 224 reads the biometric data D1 from the storage section 23, and transmits the biometric data collation instruction and biometric data D1 to the server device 6.

In step S909, the biometric authentication section 62 of the server device 6 receives the biometric data D1 of the user U and biometric data collation instruction. The server device 6 confirms whether or not the received biometric data D1 is registered in the database DB. When the biometric data of the user U is registered, the processing is advanced to step S911. When the biometric data of the user U is not registered yet, the server device 6 notifies the VR processing device 2 that the biometric data is not registered yet. The VR processing device 2 receives the notification that the biometric data is not registered yet and, in step S910, carries out biometric data registration processing.

It should be noticed that the biometric data registration processing may be carried out independent of the payment processing. For example, the biometric data registration processing may be carried out at the time of the first activation or the like of the VR system 1. Details of the biometric data registration processing will be described later in connection with FIG. 10.

In step S911, the biometric authentication section 62 of the server device 6 carries out biometric data collation processing. More specifically, the biometric authentication section 62 reads the already-registered biometric data D2 of the user U registered in the database DB, and collates the read biometric data D2 with the biometric data D1 received from the VR processing device 2. The biometric authentication section 62 transmits a notification indicating that the collation result is successful or unsuccessful to the VR processing device 2.

FIG. 10 is a flowchart exemplifying the biometric data registration processing according to this embodiment.

In step S1001, the VR processing device 2 displays the type of each of the available biometric data acquisition devices. The retrieval processing of the biometric data acquisition device which is available is identical to the processing of step S905.

In step S1002, the VR processing device 2 displays the position, direction, and type of each of the available biometric data acquisition devices which are obtained in step S1001 on the VR screen. The detection method and display method of the position and direction of the biometric data acquisition device are identical to the methods described in step S906.

In step S1003, the VR processing device 2 makes the user U select one biometric data acquisition device from among the biometric data acquisition devices displayed on the VR screen in step S1002.

It should be noted that when a biometric data acquisition device is specified in step S901, a biometric data acquisition device identical to the biometric data acquisition device specified in step S901 may automatically be specified. In this case, in step S1001 and step S1002, the biometric data acquisition device specified in step S901 is displayed on the VR screen, and the processing in step S1003 may be omitted.

In step S1004, the VR processing device 2 makes the user U input biometric data to the specified biometric data acquisition device. The input biometric data is transmitted to the VR processing device 2.

In step S1005, the VR processing device 2 receives the biometric data input to the biometric data acquisition device in step S1004. The biometric data transmission section 224 of the VR processing device 2 transmits the biometric data and a biometric data registration instruction to the server device 6.

In step S1006, the server device 6 registers the received biometric data in the database DB.

FIG. 11 is a view showing a first example of the VR screen display at the time of biometric data registration or at the time of biometric data acquisition according to this embodiment. More specifically, FIG. 11 shows the VR screen V1 to be displayed on the display section 37 in step S906 of FIG. 9 and in step S1002 of FIG. 10.

The VR screen V1 displays a biometric sensor selection screen W1 indicating available (or registration-enabled) biometric sensors. In FIG. 11, although the biometric sensor selection screen W1 is displayed on the VR screen V1 in a superimposing manner, the display method is not limited to this. For example, the VR screen V1 may be switched and the biometric sensor selection screen W1 may be displayed on the full screen.

On the biometric sensor selection screen W1, available biometric data acquisition devices and devices in which available biometric data acquisition devices are included are displayed. In the example of FIG. 11, on the biometric sensor selection screen W1, a VR headset 103, an iris sensor 103A, voiceprint sensor 103B, and vein sensor 103C included in the VR headset 103, controller 104, vein sensor 104A and fingerprint sensor 104B included in the controller 104, controller 105, fingerprint sensor 105A and vein sensor 105B included in the controller 105, sensor device 106, and voiceprint sensor 106A included in the sensor device 106 are displayed.

It should be noticed that it is desirable that the directions of the images of the devices and biometric sensors displayed on the biometric sensor selection screen W1 be changed in real time in accordance with the movement of the user U operating the devices. Further, when two or more types of biometric sensors are included, it is desirable that the biometric sensors be displayed so that the user U can easily distinguish between biometric sensors of an identical type and biometric sensors of a different type by, for example, color, shape, and the like.

The biometric sensor selection screen W2 shows a state where the vein sensor 104A is selected by the user U from among the biometric sensors displayed on the biometric sensor selection screen W1.

Selection of the biometric sensor may be carried out by, for example, the user U by operating the input section 45 of the controller 4. Further, selection of the biometric sensor may be carried out by, for example, the user U by instructing by voice through the microphone 35 of the VR headset 3.

Around the selected vein sensor 104A, a sensing-feasible area A is displayed. The sensing-feasible area indicates a range within which biometric data can be acquired by making part of the body of the user U close to the biometric sensor.

The user U inputs vein data by making, for example, his or her finger close to a position within the range of the sensing-feasible area A of the displayed vein sensor 104A.

Further, when, for example, the user changes the position and direction of the controller 4, whereby the display of the controller 104 displayed on the biometric sensor selection screen W2 changes, the display of the sensing-feasible area A also changes in accordance with the position and direction of the controller 104.

It should be noticed that when the other biometric sensor is selected too, a sensing-feasible area corresponding to the selected biometric sensor is displayed as in the above-mentioned case.

It should be noticed that the display mode of the sensing-feasible area is not limited to the mode shown in FIG. 11 as far as an area is displayed in the mode.

Figure 12:
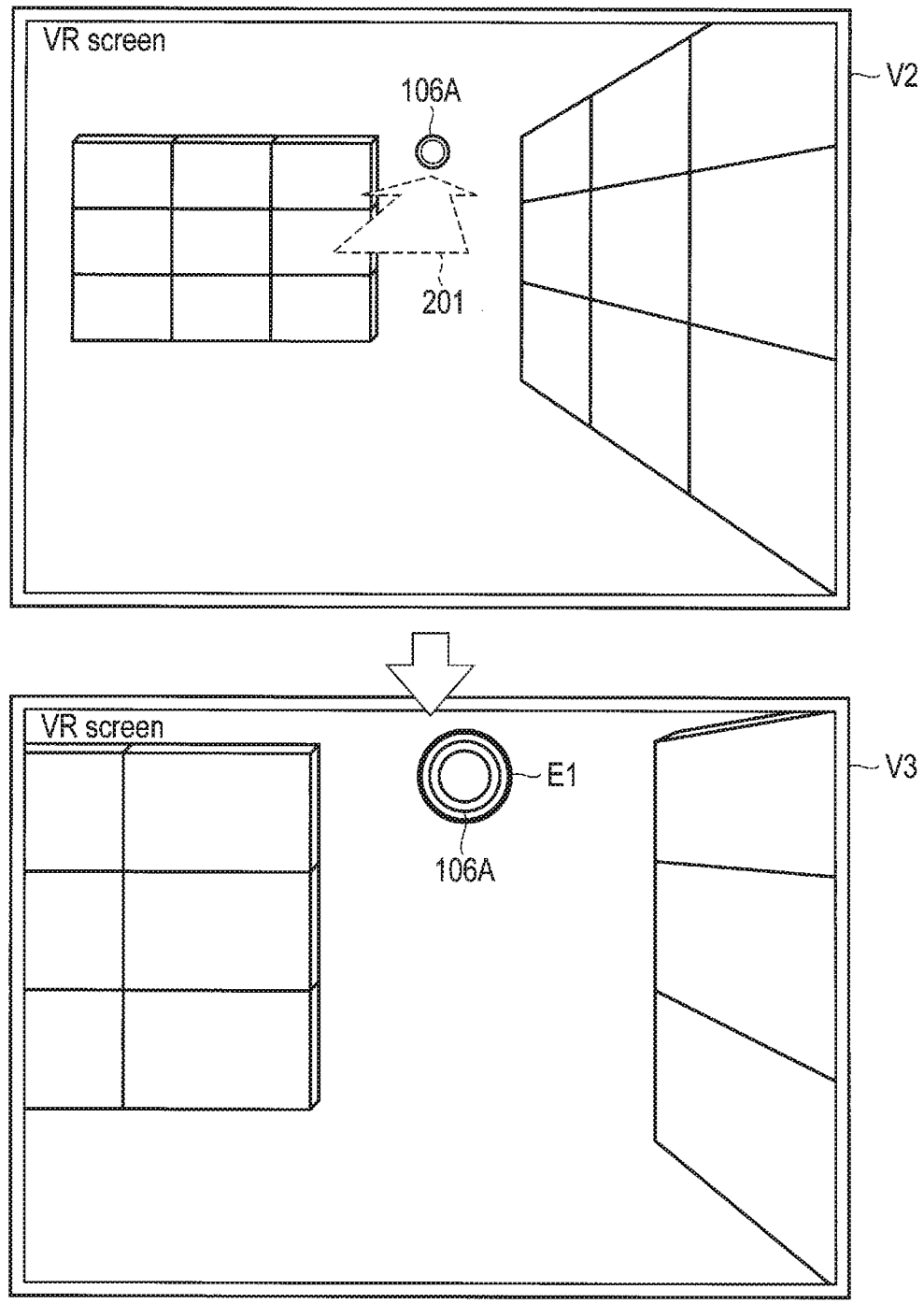
FIG. 12 is a view showing a second example of the VR screen display at the time of biometric data registration or at the time of biometric data acquisition according to the first embodiment.

FIG. 12 is a view showing a second example of the VR screen display at the time of biometric data registration or at the time of biometric data acquisition according to this embodiment.

The VR screen V2 shows a state where the voiceprint sensor 106A is selected by the user U from among the biometric sensors displayed on the biometric sensor selection screen W1 of FIG. 11.

The sensor device 106 including the voiceprint sensor 106A exists at a place separate away from the current position of the user U, and hence the VR processing device 2 guides the user U to a position at which the voiceprint sensor 106A reacts.

First, the control section 221 acquires the position of the user U. The camera 57 of the sensor device 5 shoots the user U, whereby the control section 54 or control section 221 may calculate the position and direction of the user U in the VR system 1. Alternatively, the position and direction detected by the sensor section of the VR headset 3 worn by the user U may be made the position and direction of the user U.

Next, the control section 221 determines the direction in which the user U is to be guided on the basis of the acquired position and direction of the user U, and position and direction of the voiceprint sensor 106A. The direction in which the user is to be guided is converted into data indicating the position and direction in the VR system 1, and the converted data is input to the content creation section 222.

The content creation section 222 draws an arrow 201 indicating the direction in which the user U is to be guided in the VR content on the basis of the data received from the control section 221.

It should be noted that the method of guiding the user U is not limited to the above-mentioned method. For example, the position of the voiceprint sensor 106A may be highlighted on the VR screen V2 by the content creation section 222.

The VR screen V3 shows a state where the position of the user U has become close to the position at which the voiceprint sensor 106A reacts.

When the distance between the user U and voiceprint sensor 106A has become less than or equal to a fixed value, the control section 221 notifies the user U that the voiceprint sensor 106A has become available. For example, upon receipt of the notification that the distance between the user U and voiceprint sensor 106A has become less than or equal to the fixed value from the control section 221, the content creation section 222 may depict a mark E1 at the position of the voiceprint sensor 106A of the VR content. The user U visually confirms the mark E1 in the VR content, whereby the user inputs voiceprint data to the voiceprint sensor 106A.

It should be noted that the shape and display method of the mark E1 are not limited to those shown in FIG. 12. Further, the method of notifying the user that the voiceprint sensor 106A has become available is not limited to the method described above. For example, the notification may be given to the user by voice through the speaker 36 of the VR headset 3.

FIG. 13 is a view exemplifying the VR screen display at the time of biometric data selection according to this embodiment. More specifically, FIG. 13 shows the VR screen V4 to be displayed on the display section 37 in step S901 of FIG. 9.

The VR screen V4 displays a biometric data selection screen W3. In FIG. 13, although the biometric data selection screen W3 is displayed on the VR screen V4 in a superimposing manner, the display method is not limited to this as in the case of the biometric sensor selection screen W1.

On the biometric data selection screen W3, the types of biometric data to be acquired are displayed. In the example of FIG. 13, on the biometric data selection screen W3, fingerprint data B1, facial data B2, iris data B3, vein data B4, and voiceprint data B5 are displayed as selectable items.

When one of the above-mentioned items is selected by the user U, an indication that an item has been selected is displayed on the VR screen V4. For example, on the VR screen V4, a mark E2 may be displayed around the selected item.

It should be noted that selection of the biometric data may be carried out by the user U by operating the input section 45 of the controller 4. Further, selection of the biometric data may be carried out by, for example, the user U by instructing by voice through the microphone 35 of the VR headset 3.

It should be noted that the shape and display method of the mark E2 are not limited to those exemplified in FIG. 13.

Figure 14:
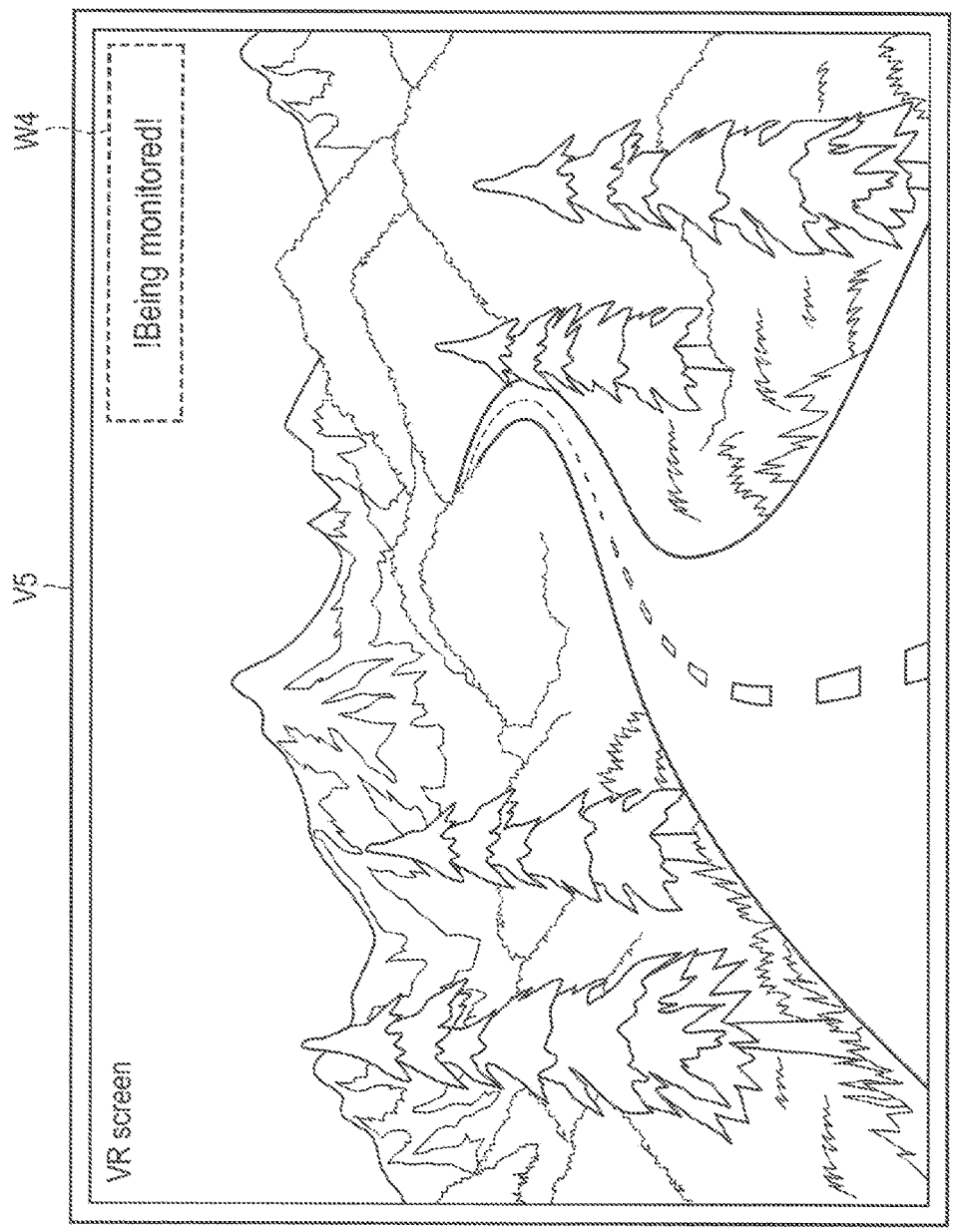
FIG. 14 is a view exemplifying the VR screen display at the time of content sharing according to the first embodiment.

FIG. 14 is a view exemplifying the VR screen display at the time of content sharing according to this embodiment. More specifically, FIG. 14 shows the VR screen V5 to be displayed on the display section 37 when the content sharing section 225 is transmitting content to the mobile terminal 8.

The VR screen V5 includes the screen display W4. The screen display W4 is an image or characters indicating that the content is shared with the mobile terminal 8.

It should be noted that the screen display W4 can be displayed at an arbitrary position on the VR screen V5 which can be recognized by the user. Further, the screen display W4 may be moved or erased automatically or by the operation of the user U.

In this embodiment described above, in the VR system 1, the position and direction of the biometric sensor can be displayed on the VR screen. Thereby, the user U can purchase a commercial product on the VR screen and, even when acquisition of biometric data is needed for payment, can input biometric data without taking off the VR headset 3.

In this embodiment, biometric data is used for payment, and hence security of the payment is ensured.

In this embodiment, the mobile terminal 7 owned by the user U can be added to the VR system 1 in place of, for example, the controller 4. Thereby, it is possible to construct a system from a normal virtual reality system and mobile telephone, and reduce the cost.

In this embodiment, even when the positions of the biometric data acquisition device and user U are separate from each other, the VR system 1 guides the user U to a position at which the user U can input biometric data. Thereby, the convenience of the user U inputting the biometric data is further enhanced.

In this embodiment, it is made possible for the VR content displayed on the display section 37 of the headset 3 to be output also to the display section 75 of the mobile terminal 8 authenticated by the VR system 1. Thereby, when the VR system 1 is shared among family members, it is possible for the parent to grasp, for example, what type of game his or her child wearing the VR headset 3 plays by using the parent's own mobile terminal 8, and prevent his or her child from being spoiled by harmful content. Further, it is possible for a person not wearing the VR headset 3 to share the VR content, and it is also possible to enhance the amusement nature.

Second Embodiment

In this embodiment, a VR system in which an attribute of a character (avatar) made appear on the VR screen is determined by using biometric data acquired from the user of the VR system will be described below.

The VR system used in this embodiment is identical to the VR system 1 in the first embodiment.

Figure 15:
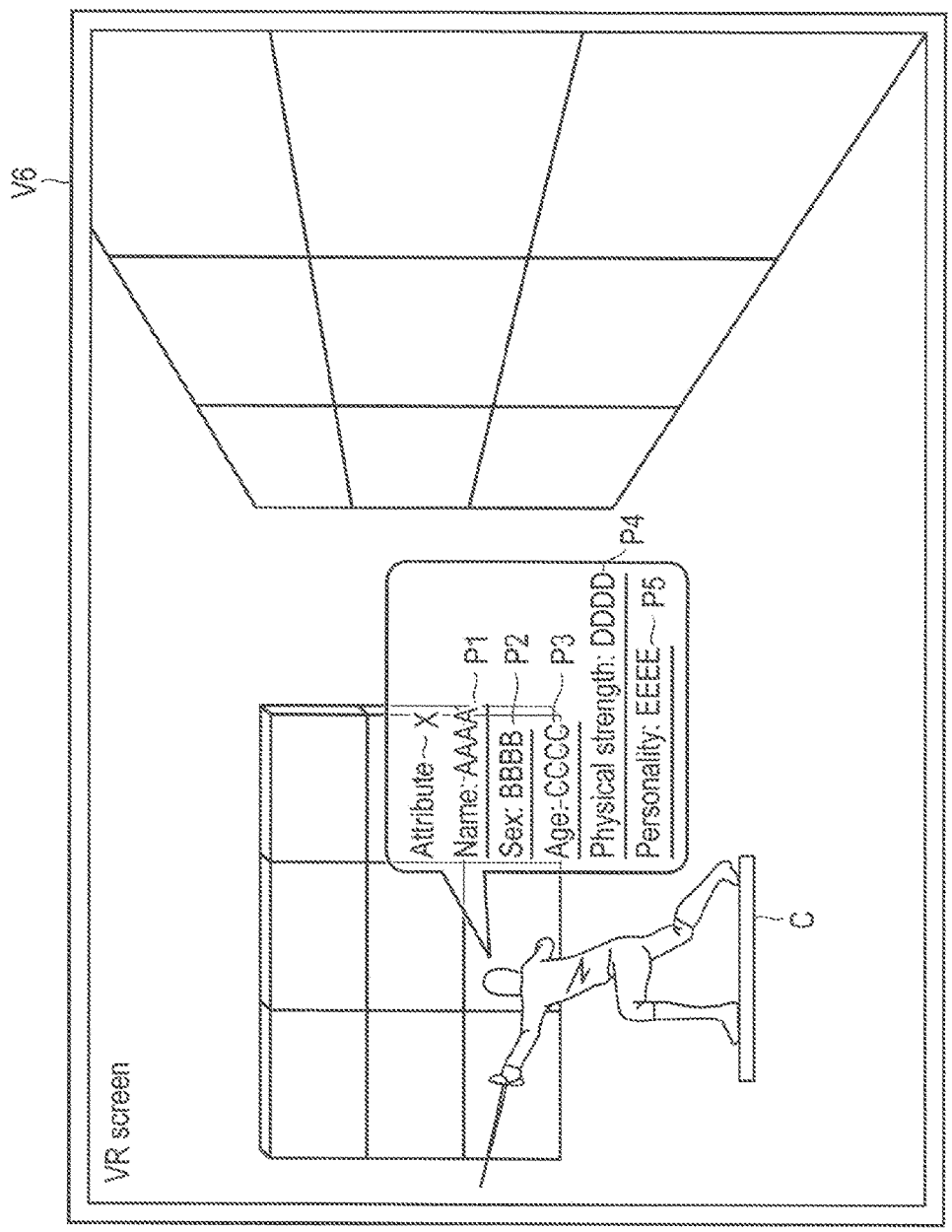
FIG. 15 is a view exemplifying the VR screen display at the time of character display according to a second embodiment.

FIG. 15 is a view exemplifying the VR screen display at the time of character display according to a second embodiment.

The VR screen V6 displays a character C corresponding to the user U, and attribute X of the character C. The attribute X need not be displayed on the VR screen V6 at all times, and may be displayed only when a display instruction to display the attribute X is received from the user U.

The attribute X includes the attribute of the character C. For example, the attribute X includes a name P1, sex P2, age P3, physical strength P4, and personality P5. The attribute of the character C may include items other than these items.

The image of the character C may be configured to change in appearance and state according to the contents of the items of the attribute X. For example, the appearance of the character C may change to conform to, for example, the sex P2 or age P3, the posture of the character C may change according to the physical strength P4, and the facial expressions of the character C may change according to the personality P5.

The items of the attribute X may be updated on the basis of a result of analysis of the biometric data of the user U carried out by the VR system 1 each time the user U carries out biometric authentication.

Figure 16:
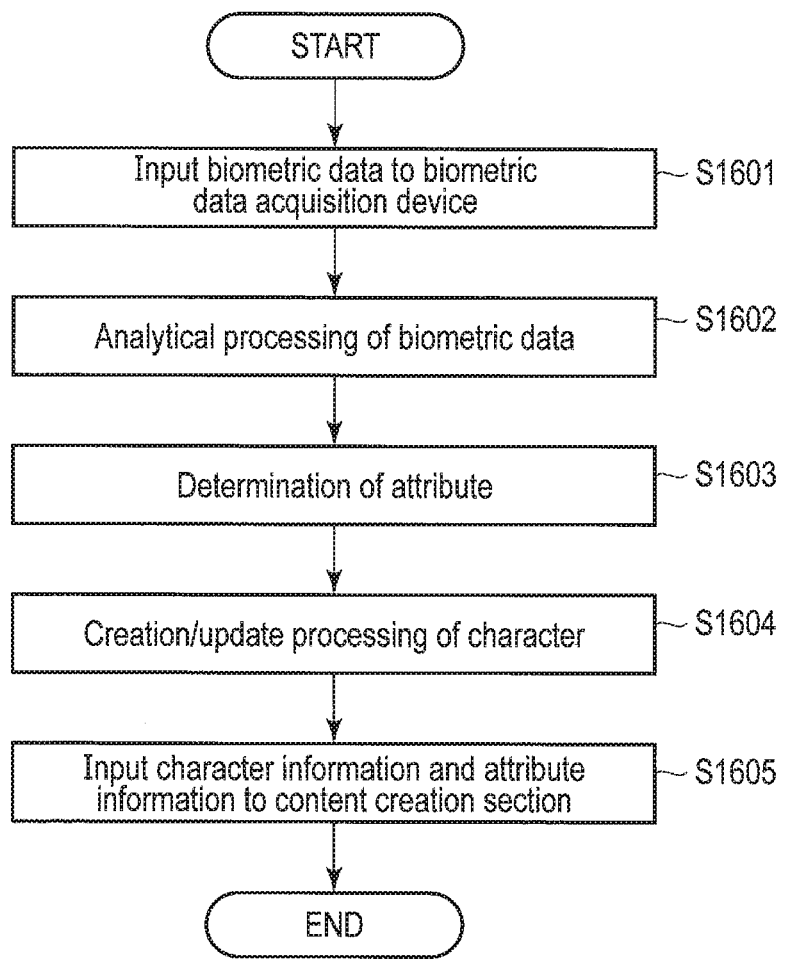
FIG. 16 is a flowchart exemplifying an attribute determination processing according to the second embodiment.

FIG. 16 is a flowchart exemplifying the attribute determination processing according to the second embodiment.

In step S1601, biometric data of the user U is input to an arbitrary biometric data acquisition device in the VR system 1. The timing at which the biometric data of the user U is input may be step S904 or step S907 of FIG. 9 or step S1004 of FIG. 10, and the biometric data may be input at timing other than the timing described above. The biometric data acquired by the biometric data acquisition device is transmitted to the VR processing device 2.

In step S1602, the control section 221 of the VR processing device 2 receives the biometric data input by the user U, and carries out analytical processing. For example, when the biometric data is voiceprint data, the control section 221 determines the age and sex of the user U on the basis of the pitch and tone quality of the voice. For example, when the biometric data is facial data, the control section 221 determines the personality of the user U by reading the facial expressions. It should be noticed that the analytical processing to be carried out by the control section 221 is not limited to the above.

In step S1603, the control section 221 carries out determination of the attribute of the character C on the basis of the analysis result of the biometric data obtained in step S1602. The type (item) of the attribute may be determined in advance by the user U or may be automatically created by the control section 221 on the basis of the analysis result.

In step S1604, the control section 221 carries out creation processing or update processing of the character C on the basis of the attribute obtained in step S1603. It should be noted that at the time of first creation of the character C, an image constituting the basic state of the character C may be selected in advance by the user U. Alternatively, the control section 221 may automatically create the character C on the basis of the attribute.

In step S1605, the control section 221 inputs the character information and attribute information to the content creation section 222. The content creation section 222 creates VR content including display of the character C and attribute X on the basis of the input character information and attribute information. The VR content is transmitted to the VR headset 3 by the content transmission section 223, and is displayed on the display section 37.

In this embodiment described above, it is possible to automatically display the character C in which the attribute X included in the biometric data is reflected on the VR screen by using the biometric data acquired from the user U. Thereby, it becomes possible to create a character C in which the individual character of the user U is reflected, and it becomes easy to distinguish an individual on the network through the VR. Further, by making the individual character of the user U reflected in the character, it is possible to enhance the amusement nature.

Third Embodiment

In recent years, systems for carrying out automatic diagnosis of diseases on the basis of input medical examination data or the like by using Artificial Intelligence (AI) are developed. However, collection of medical examination data items for utilizing such a diagnosis system is a burden on the user, and hence a technique for enhancing the convenience of the user is desired.

In this embodiment, a diagnosis system in which the user of the VR system accumulates biometric data daily input by the user to the VR system, the user inputs the accumulated biometric data items to the diagnosis system, and receives the result, whereby a simplified diagnostic result of a disease can be acquired without the user being conscious of collection of data necessary for utilization of the diagnosis system is proposed. Further, a hospital and medical section available for the user are proposed from the diagnostic result, whereby it is possible to further enhance the convenience of the user.

FIG. 17 is a block diagram exemplifying the configuration of an automatic diagnosis system according to a third embodiment.

The automatic diagnosis system 11 includes a VR system 1A, diagnosis server device 9, and reservation system 10.

A VR processing device 2 included in the VR system 1A includes a storage section 23. The storage section 23 includes biometric data D1, and position information 233.

The biometric data D1 stores therein biometric data input by the user U to any one of the biometric data acquisition devices 25, 33, 43, 53, and 73.

The position information 233 is used by, for example, the diagnosis server device 9 to extract a hospital in which the user U can have a consultation.

The position information 233 may be, for example, an address registered in the VR system 1 in advance by the user U or, when the VR processing device 2 or mobile terminal 7 is provided with the Global Positioning System (GPS), may be the position indicated by the GPS when the screen display T1 to be described later is displayed. The acquisition method of the position information 233 is not limited to the method described above.

It should be noted that the other configurations of the VR system 1A according to this embodiment are identical to the configuration of the VR system 1 in the first embodiment.

The diagnosis server device 9 includes a storage section 91, control section 92, and communication section 93.

The storage section 91 includes hospital information 911.

The hospital information 911 is, for example, information correlating a disease name, hospital and medical section capable of coping with the disease name, and location of the hospital with each other. The control section 92 carries out control of the whole diagnosis server device 9. The control section 92 executes diagnosis processing on the basis of, for example, the biometric data of the user U, and obtains a disease name as the diagnostic result. Furthermore, the control section 92 creates a list of hospitals and medical sections capable of coping with the disease names on the basis of the hospital information 911, diagnostic results, and position information 233 received from the VR processing device 2, and transmits the list to the VR processing device.

The communication section 93 transmits/receives commands, addresses, data items, information items, instructions, signals, and the like to/from, for example, the VR processing device 2 through the network N.

The reservation system 10 is a general hospital reservation system capable of accepting a reservation for the date and time of consultation from a patient or the like. The reservation system 10 is realized by, for example, a program or the like operating on a server device provided in a hospital.

Figure 18:
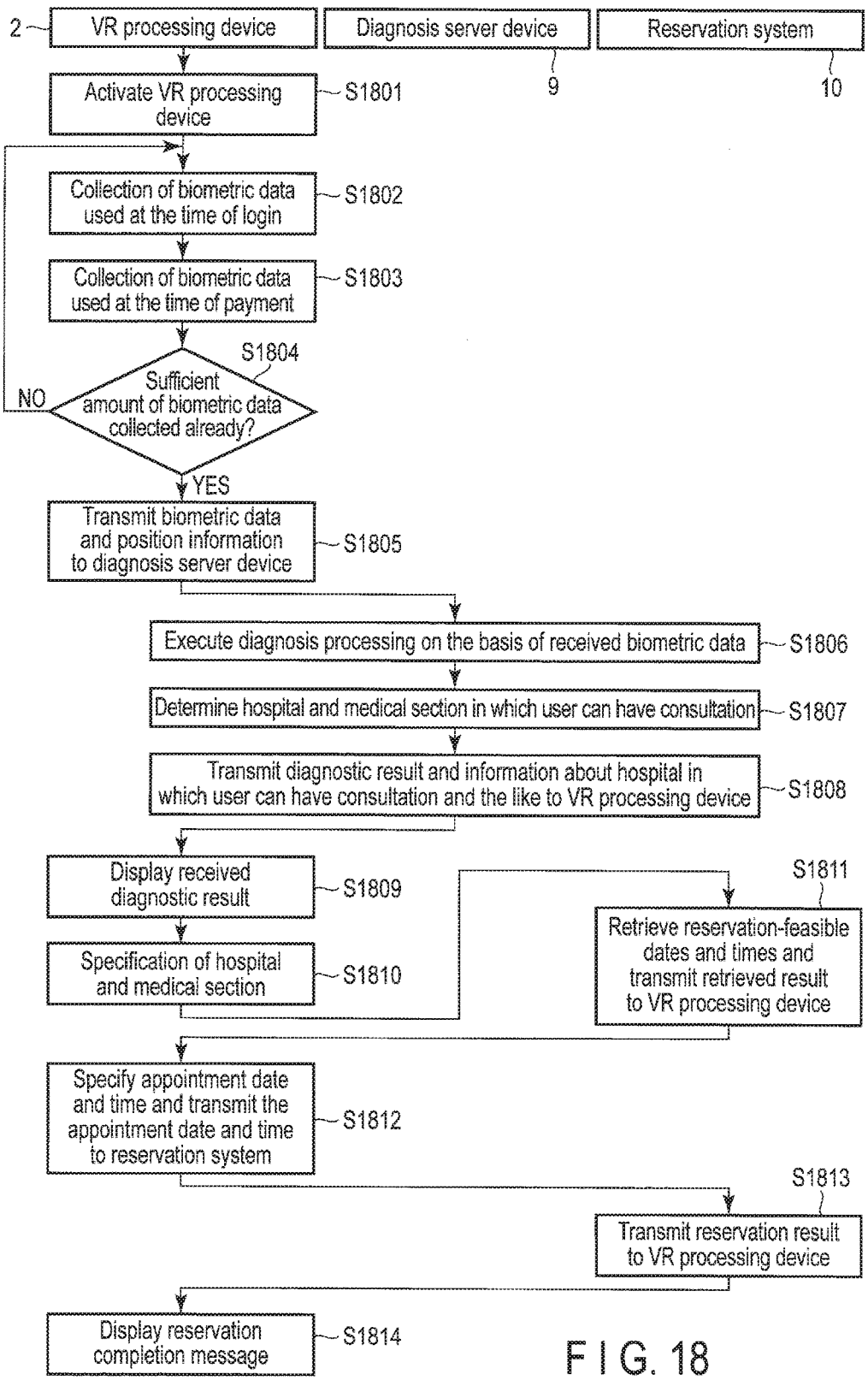
FIG. 18 is a flowchart exemplifying a processing of the automatic diagnosis system according to the third embodiment.

FIG. 18 is a flowchart exemplifying the processing of the automatic diagnosis system 11 according to this embodiment.

In step S1801, the VR processing device 2 is activated. Power is also supplied to the VR headset 3, controllers 4, and sensor devices 5 which are connected to the VR processing device 2, and the devices become in a state in which they can be operated by the user U.

In step S1802, when input of biometric data is required at the time of login to the VR system 1A, the VR processing device 2 carries out collection of biometric data items used at the time of login. More specifically, the VR processing device 2 receives the biometric data input by the user U, at the time of login, to any one of the biometric data acquisition devices 25, 33, 43, 53, and 73 from any one of the VR headset 3, controllers 4, sensor devices 5, and mobile terminal 7 including these biometric data acquisition devices, and stores the received biometric data in the storage section 23.

It should be noted that login to the VR system 1A may be carried out by the user U to the VR processing device 2 or may be carried out by the user U to the mobile terminal 7.

In step S1803, the VR processing device 2 carries out collection of the biometric data used at the time of payment each time payment processing is carried out in the VR system 1A. The collection method of the biometric data is identical to that in step S1802.

In step S1804, the VR processing device 2 confirms whether or not the amount and types of the biometric data D1 stored in the storage section 23 are sufficient to such a degree that the amount and types of the biometric data D1 can be input to the diagnosis server device 9. When it is determined by the VR processing device 2 that the amount and types of the biometric data D1 are not sufficient, the processing is returned to step S1802, and collection of the biometric data is continued. Further, when it is determined by the VR processing device 2 that the amount and types of the biometric data D1 are sufficient, the processing is advanced to step S1805.

In step S1805, the VR processing device 2 acquires the position information 233 of the VR processing device, and stores the position information 233 in the storage section 23. Further, the VR processing device 2 transmits the biometric data D1 and position information 233 to the diagnosis server device 9.

In step S1806, the diagnosis server device 9 executes diagnosis processing on the basis of the biometric data D1 received from the VR processing device 2, and obtains a diagnostic result. The diagnostic result may be, for example, a disease name or the like. The diagnosis processing may be carried out by using Artificial Intelligence (AI) or may be carried out by using other arbitrary algorithms.

In step S1807, the diagnosis server device 9 retrieves and extracts hospitals within a range available for the user U. Furthermore, the diagnosis server device 9 determines a hospital and medical section in which the user U can have a consultation on the basis of the diagnostic result, extracted hospitals, and hospital information 911.

In step S1808, the diagnosis server device 9 transmits data including the diagnostic result and hospital and medical section in which the user U can have a consultation obtained in step S1806 and step S1807 to the VR processing device 2.

In step S1809, the VR processing device 2 displays the information about the diagnostic result, hospital, medical section, and the like on the display section 37 of the VR headset 3 or display section 75 of the mobile terminal 7 on the basis of the data received from the diagnosis server device 9. Details of the screen displayed on the display section 37 or 75 will be described later in connection with FIG. 19.

In step S1810, the VR processing device 2 makes the user U specify the hospital and medical section displayed on the display section 37 or 75. The data indicating the hospital and medical section specified by the user U is transmitted to the reservation system 10.

In step S1811, the reservation system 10 retrieves the reservation-feasible dates and times of the hospital and medical section specified in step S1810, and transmits the retrieved result to the VR processing device 2.

In step S1812, the VR processing device 2 displays the reservation-feasible dates and times on the display sections 37 and 75, and makes the user U specify the appointment date and time. The information about the appointment date and time specified by the user U is transmitted to the reservation system 10.

In step S1813, the reservation system 10 transmits the reservation result to the VR processing device 2 to complete the reservation.

In step S1814, the VR processing device 2 notifies the user that the reservation is completed. More specifically, for example, a reservation completion message is displayed on the display sections 37 and 75.

It should be noticed that the VR processing device 2 may transmit the diagnostic result to the reserved hospital, for example, after the reservation is completed.

Figures 19, 20:
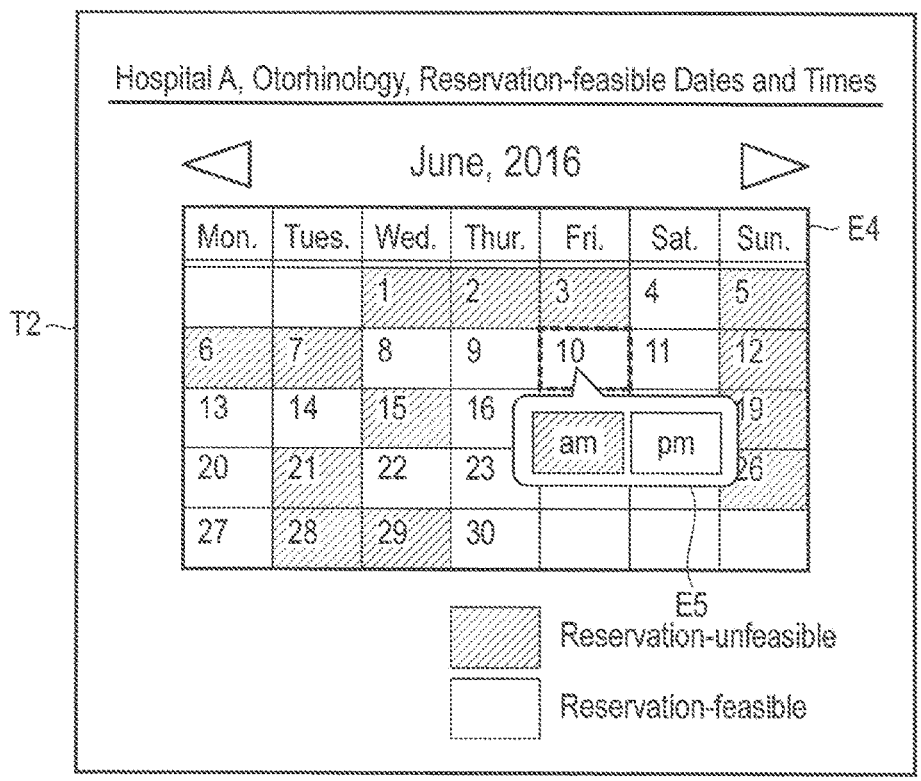
FIG. 19 is a view showing a first example of the screen display in the automatic diagnosis system according to the third embodiment.
FIG. 20 is a view showing a second example of the screen display in the automatic diagnosis system according to the third embodiment.

FIG. 19 is a view showing a first example of the screen display in the automatic diagnosis system 11 according to this embodiment. More specifically, FIG. 19 shows the diagnostic result and list of hospitals and medical sections in which the user can have a consultation to be displayed on the display sections 37 and 75 in step S1809 of FIG. 18.

The screen display T1 includes disease name Q1, hospital Q2, medical section Q3, and address Q4.

Disease name Q1 indicates a disease name based on the received diagnostic result.

Hospital Q2 indicates a name of a hospital in which a consultation associated with the disease name Q1 can be obtained.

Medical section Q3 indicates a medical section in which the user U can have a consultation as to the disease name Q1 in the hospital Q2. It is desirable that the display of medical sections included in the medical section Q3 be selectable by the user U. The control section 221 or control section 741 displays a reservation screen as to the medical section selected by the user U. The selected medical section is, highlighted as in the case of, for example, a display E3.

Address Q4 is an address indicating the location of the information about hospital Q2 and medical section Q3. Address may be, for example, Uniform Resource Locator (URL) or the like.

It should be noted that the items included in the screen display T1 are not limited to those described above. Further, the screen display T1 may be displayed in forms other than the tabular form. The display of addresses included in address Q4 may be selectable by the user U. In this case, the control section 221 or control section 741 may display a web page or the like correlated with address Q selected by the user U.

FIG. 20 is a view showing a second example of the screen display in the automatic diagnosis system 11 according to this embodiment. More specifically, FIG. 20 shows the reservation screen displayed on the display sections 37 and 75 in step S1812 of FIG. 18. FIG. 20 shows the screen displayed when "otorhinological section of hospital A" is selected (see the display E3) on the screen display T1 of FIG. 19.

The screen display T2 includes a date selection display E4. The date selection display E4 may be, for example, calendar display or may be list display.

It is desirable that in the date selection display E4, reservation-feasible dates and reservation-unfeasible dates be explicitly indicated. When a reservation-feasible date is selected by the user U, the control section 221 or control section 741 may further display a time-slot selection display E5. The user U further selects a reservation-feasible time-slot to thereby complete designation of the reservation date and time. It should be noted that the time-slot selection display E5 may be, for example, pop-up display, list display or other display forms.

In this embodiment, the screen display T1 and screen display T2 may be displayed by an application installed in the VR processing device 2 or mobile terminal 7. In this case, the processing of retrieving and displaying hospital Q2 and medical section Q3 and screen display processing may be carried out by the application by using the processor 22 and processor 74.

In this embodiment described above, the automatic diagnosis system 11 collects biometric data to be input by the user U to the VR system 1A when the user U logs into the VR system 1A or carries out payment, and transmits the collected biometric data items to the diagnosis server device 9. Thereby, it becomes possible for the user U to acquire the diagnostic result without consciously carrying out collection of data to be input to the diagnosis server device 9, and the convenience of the user is enhanced. Further, the automatic diagnosis system 11 selects an optimum hospital and medical section on the basis of the diagnostic result, carries out hospital reservation, and transmits the diagnostic result obtained from the diagnosis server device 9 to the hospital. Thereby, further it is possible not only enhance the convenience of the user but also contribute to prevention of medical errors and shortening of the consultation hours.

It should be noted that in this embodiment, the automatic diagnosis system 11 is applicable not only to diagnosis of the disease name of the user U but also to all types of diagnoses. For example, when the automatic diagnosis system 11 is to be applied to medical examination, the automatic diagnosis system 11 may replace disease name Q1 and medical section Q3 among the contents of the screen display T1 with inspection items and detailed inspection medical institution as items to be correlated with medical examination to thereby present the items to the user U.

Further, in this embodiment, in the automatic diagnosis system 11, a different type of information processing device or system capable of acquiring the biometric data D1 and capable of acquiring and storing the position information 233 may be included in place of the VR system 1.

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A virtual reality system comprising:
a controller configured to accept an instruction from a user;
a first information processing device configured to create virtual reality content according to the instruction received from the controller;
a virtual reality headset worn by the user and configured to display the virtual reality content received from the first information processing device to the user;
a biometric data acquisition device configured to acquire biometric data of the user;
a first sensor configured to create first position information indicating a position of the biometric data acquisition device, and first direction information indicating a direction of the biometric data acquisition device, and transmit the first position information and the first direction information to the first information processing device;
a second sensor configured to create second position information indicating a position of the virtual reality headset, and second direction information indicating a direction of the virtual reality headset, and transmit the second position information and the second direction information to the first information processing device; and
a second information processing device communicatively coupled to the first information processing device via a network, wherein
the first information processing device adds, when a payment instruction is received from the controller, an image making the user wearing the virtual reality headset recognize a position and a direction of the biometric data acquisition device and a range within which the biometric data can be acquired by the biometric data acquisition device, and prompting the user wearing the virtual reality headset to input biometric data by means of the biometric data acquisition device to the virtual reality content on the basis of the first position information and the first direction information received from the first sensor, and the second position information and the second direction information received from the second sensor, transmits the virtual reality content to the virtual reality headset, and receives, after the virtual reality content including the image prompting the user to input the biometric data is displayed by the virtual reality headset, the biometric data of the user from the biometric data acquisition device, and transmit the biometric data to the second information processing device, and the second information processing device collates the biometric data received from the first information processing device, and already-registered biometric data of the user stored in a storage device referred to by the second information processing device with each other and, when the collation is successful, permits the payment instruction.

2. The virtual reality system of claim 1, further comprising a mobile terminal including the first sensor and the biometric data acquisition device, wherein the mobile terminal transmits the first position information and the first direction information to the first information processing device, and transmits the biometric data of the user to the first information processing device.

3. The virtual reality system of claim 1, wherein the first information processing device carries out authentication of a third information processing device capable of communicating with the first information processing device, and operated by another user different from the user and, when the authentication of the third information processing device is successful, permits communication between the first information processing device and the third information processing device, converts the virtual reality content into content corresponding to the third information processing device, and transmits the converted content to the third information processing device, the third information processing device includes a display configured to display the virtual reality content received from the first information processing device, the first information processing device adds, when the converted content is transmitted to the third information processing device, another image or characters indicating that the converted content is shared to the virtual reality content, and transmits the virtual reality content including the image or the characters indicating that the converted content is shared to the virtual reality headset.

4. The virtual reality system of claim 1, wherein the first information processing device adds the image guiding the user to the biometric data acquisition device to the virtual reality content on the basis of a difference between the first position information and the second position information and a difference between the first direction information and the second direction information.

5. The virtual reality system of claim 1, wherein the first information processing device determines an attribute of a character corresponding to the user on the basis of at least one of the biometric data and the already-registered biometric data, and creates the virtual reality content according to the attribute.

6. An information processing system comprising:

the virtual reality system of claim 1; and a diagnosis processing device, wherein the first information processing device stores therein historical data of the biometric data received from the biometric data acquisition device, and third position information indicating a position of the user, and transmits the historical data and the third position information to the diagnosis processing device, the diagnosis processing device stores therein hospital information in which disease names, hospitals, and medical sections capable of coping with the disease names, and locations of the hospitals are correlated with each other, and receives the historical data and the third position information from the first information processing device, executes diagnosis processing on the basis of the historical data, creates a list of hospitals and medical sections capable of coping with a result of the diagnosis processing on the basis of the hospital information, the result of the diagnosis processing, and the third position information, and transmits the list to the first information processing device, and the first information processing device displays the list received from the diagnosis processing device on the display.

7. The information processing system of claim 6, wherein the first information processing device makes the user select one of the hospitals and one of the medical sections included in the list displayed on the display, and transmits medical section information indicating a selected medical section to a reservation system of the selected hospital, the reservation system receives the medical section information from the first information processing device, and transmits reservation-feasible dates and times of the medical section indicated by the medical section information to the first information processing device, and the first information processing device displays the reservation-feasible dates and times received from the reservation system on the display, and transmits a date and time selected by the user to the reservation system.

8. The virtual reality system of claim 1, wherein the first information processing device adds a first image indicating a position and a direction with respect to the virtual reality headset and a type of available biometric data acquisition devices in real time, and a second image indicating, in accordance with a change of the first image, a range within which the biometric data can be acquired by the biometric data acquisition device.

* * * * *